US010583032B2

(12) United States Patent
Rogers

(10) Patent No.: US 10,583,032 B2
(45) Date of Patent: *Mar. 10, 2020

(54) ORAL ORTHOTIC SYSTEMS, DEVICES AND METHODS FOR USE IN CONNECTION WITH SLEEP-DISORDERED BREATHING

(71) Applicant: AMERICAN DENTAL SLEEP MEDICINE IP, LLC, Wexford, PA (US)

(72) Inventor: Robert Rogers, Wexford, PA (US)

(73) Assignee: AMERICAN DENTAL SLEEP MEDICINE, LLC, Hollidaysburg, PA (US)

( * ) Notice: Subject to any disclaimer, the term of this patent is extended or adjusted under 35 U.S.C. 154(b) by 213 days.

This patent is subject to a terminal disclaimer.

(21) Appl. No.: 15/446,893

(22) Filed: Mar. 1, 2017

(65) Prior Publication Data

US 2017/0172785 A1 Jun. 22, 2017

Related U.S. Application Data

(63) Continuation of application No. 14/347,800, filed as application No. PCT/US2012/058165 on Sep. 29, 2012, now Pat. No. 9,615,964.

(60) Provisional application No. 61/541,336, filed on Sep. 30, 2011, provisional application No. 61/590,600, filed on Jan. 25, 2012.

(51) Int. Cl.
*A61F 5/56* (2006.01)
*A61C 7/08* (2006.01)
*A61C 7/36* (2006.01)

(52) U.S. Cl.
CPC ............... *A61F 5/566* (2013.01); *A61C 7/08* (2013.01); *A61C 7/36* (2013.01); *A61F 5/56* (2013.01); *Y10T 29/49567* (2015.01)

(58) Field of Classification Search
CPC .... A61F 5/56; A61F 5/566; A61C 7/00; A61C 7/08; A61C 7/36; A63B 71/085
USPC ......... 128/848, 859, 861; 433/6, 18, 19, 140
See application file for complete search history.

(56) References Cited

U.S. PATENT DOCUMENTS

| | | |
|---|---|---|
| 1,652,910 A | 12/1927 | Psayla |
| 2,299,285 A | 10/1942 | Taylor |
| 4,330,273 A | 5/1982 | Kesling |
| 4,368,040 A | 1/1983 | Weissman |
| 4,459,107 A | 7/1984 | Weissman |

(Continued)

FOREIGN PATENT DOCUMENTS

| | | |
|---|---|---|
| DE | 202008011841 | 11/2008 |
| DE | 202009003999 | 7/2009 |

(Continued)

*Primary Examiner* — Keri J Nelson
(74) *Attorney, Agent, or Firm* — Bartony & Associates, LLC

(57) ABSTRACT

A method of forming oral orthotic systems includes providing an upper dental member adapted to be placed in connection with upper dentition of the patient, providing a lower dental member adapted to be placed in connection with lower dentition of the patient and providing a plurality of posterior mounting structures. Each of the posterior mounting structure is configured to be attached to one of the upper dental member or the lower dental member at a posterior, buccal position thereon. Force may be applied to the mandible of the patient via at least one of a plurality of different types mechanisms via attachment of a component of a selected type mechanism to at least one of the posterior mounting structures.

18 Claims, 20 Drawing Sheets

(56) References Cited

U.S. PATENT DOCUMENTS

| | | |
|---|---|---|
| 5,183,388 A | 2/1993 | Kumar |
| 5,267,862 A | 12/1993 | Parker |
| 5,313,960 A | 5/1994 | Tomasi |
| 5,365,945 A | 11/1994 | Halstrom |
| 5,378,147 A | 1/1995 | Mihailowitsch |
| 5,409,017 A | 4/1995 | Lowe |
| 5,467,783 A | 11/1995 | Meade |
| 5,499,633 A | 3/1996 | Fenton |
| 5,562,106 A | 10/1996 | Heeke |
| 5,570,704 A | 11/1996 | Buzzard |
| 5,601,093 A | 2/1997 | Sheehan |
| 5,611,355 A | 3/1997 | Hilsen |
| 5,642,737 A | 7/1997 | Parks |
| 5,682,903 A | 11/1997 | Meade |
| 5,692,521 A | 12/1997 | Leasure-Nelson |
| 5,755,219 A | 5/1998 | Thornton |
| 5,794,627 A | 8/1998 | Frantz |
| 5,829,441 A | 9/1998 | Kidd |
| 5,823,193 A | 10/1998 | Singer |
| 5,823,194 A | 10/1998 | Lampert |
| 5,868,138 A | 2/1999 | Halstrom |
| 5,879,157 A | 3/1999 | Scheu |
| 5,919,042 A | 7/1999 | Williams |
| 5,941,247 A | 8/1999 | Keane |
| 5,947,724 A | 9/1999 | Frantz |
| 6,012,920 A | 1/2000 | Woo |
| 6,041,784 A | 3/2000 | Halstrom |
| 6,055,986 A | 5/2000 | Meade |
| 6,099,304 A | 8/2000 | Carter |
| 6,109,265 A | 8/2000 | Frantz |
| 6,161,542 A | 12/2000 | Halstrom |
| 6,170,485 B1 | 1/2001 | Orrico |
| 6,325,064 B1 | 12/2001 | Thornton |
| 6,418,933 B1 | 7/2002 | Strong |
| 6,526,982 B1 | 3/2003 | Strong |
| 6,604,527 B1 | 8/2003 | Palmisano |
| 6,729,335 B1 | 5/2004 | Halstrom |
| 6,769,910 B1 | 8/2004 | Pantino |
| 6,845,774 B2 | 1/2005 | Gaskell |
| 7,146,982 B2 | 12/2006 | Mousselon |
| 7,520,281 B1 | 4/2009 | Nahabedian |
| 7,637,262 B2 | 12/2009 | Bailey |
| 7,712,468 B2 | 5/2010 | Hargadon |
| 7,757,693 B2 | 7/2010 | Toussaint |
| 7,987,854 B2 | 8/2011 | Arni |
| 8,074,659 B2 | 12/2011 | Hanna |
| 8,136,529 B2 | 3/2012 | Kelly |
| 8,205,617 B2 | 6/2012 | Scarberry |
| 2002/0000230 A1 | 1/2002 | Gaskell |
| 2003/0059737 A1 | 3/2003 | Hall |
| 2004/0177853 A1 | 9/2004 | Kownacki |
| 2005/0028826 A1 | 2/2005 | Palmisano |
| 2005/0028827 A1 | 2/2005 | Halstrom |
| 2005/0199247 A1 | 9/2005 | Garabadian |
| 2007/0079833 A1 | 4/2007 | Lamberg |
| 2007/0224567 A1 | 9/2007 | Robson |
| 2007/0283967 A1 | 12/2007 | Bailey |
| 2007/0292819 A1 | 12/2007 | Scarberry |
| 2008/0060659 A1 | 3/2008 | Bonato |
| 2008/0176185 A1 | 7/2008 | Williams |
| 2008/0199824 A1 | 8/2008 | Hargadon |
| 2009/0032030 A1 | 2/2009 | Callender |
| 2009/0036889 A1 | 2/2009 | Callender |
| 2009/0090371 A1 | 4/2009 | Toussaint |
| 2010/0043805 A1 | 2/2010 | Kelly |
| 2010/0065066 A1 | 3/2010 | Hamburg |
| 2010/0095970 A1 | 4/2010 | Katz |
| 2010/0139666 A1 | 6/2010 | Bonnaure |
| 2010/0239995 A1 | 9/2010 | Williams |
| 2010/0242969 A1 | 9/2010 | Lyons |
| 2010/0242970 A1 | 9/2010 | Schmitt-Bylandt |
| 2010/0307511 A1 | 9/2010 | Meade |
| 2010/0261133 A1 | 10/2010 | Lax |
| 2011/0000495 A1 | 1/2011 | Ash |
| 2011/0088701 A1 | 4/2011 | Thornton |
| 2011/0155144 A1 | 6/2011 | Tousssaint |
| 2011/0259345 A1 | 10/2011 | Cullen |
| 2011/0277774 A1 | 11/2011 | Connell |
| 2011/0311936 A1 | 12/2011 | Marie-Catherine |
| 2012/0186589 A1 | 7/2012 | Singh |

FOREIGN PATENT DOCUMENTS

| | | |
|---|---|---|
| EP | 0254918 | 2/1988 |
| EP | 2269543 | 1/2011 |
| WO | WO03034957 | 5/2003 |
| WO | WO2011017813 | 2/2011 |
| WO | WO2013049751 | 4/2013 |

Fig. 1B
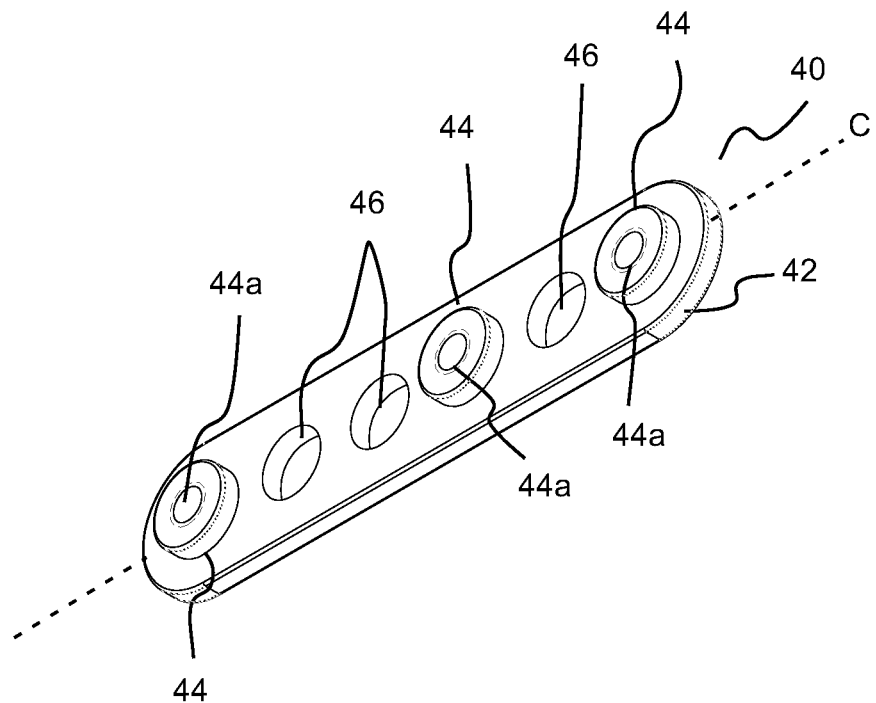
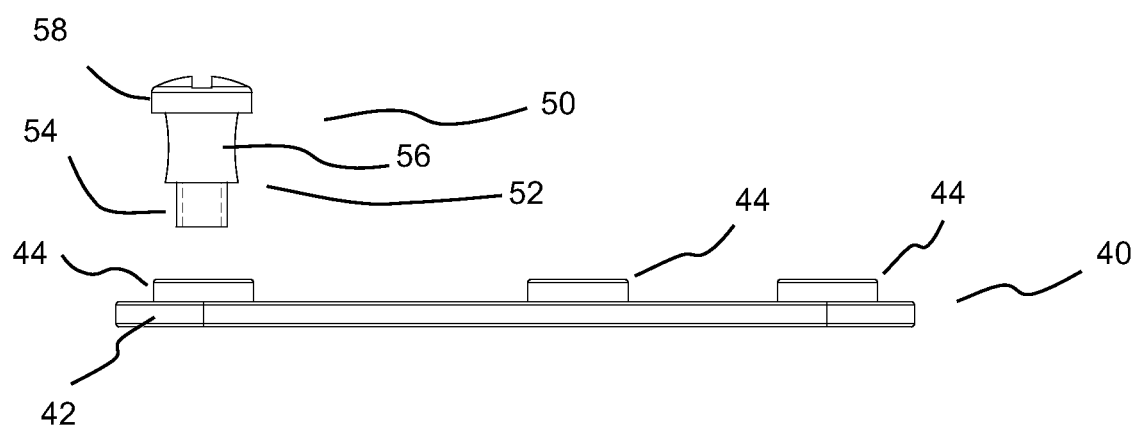
Fig. 1C

Fig. 2C
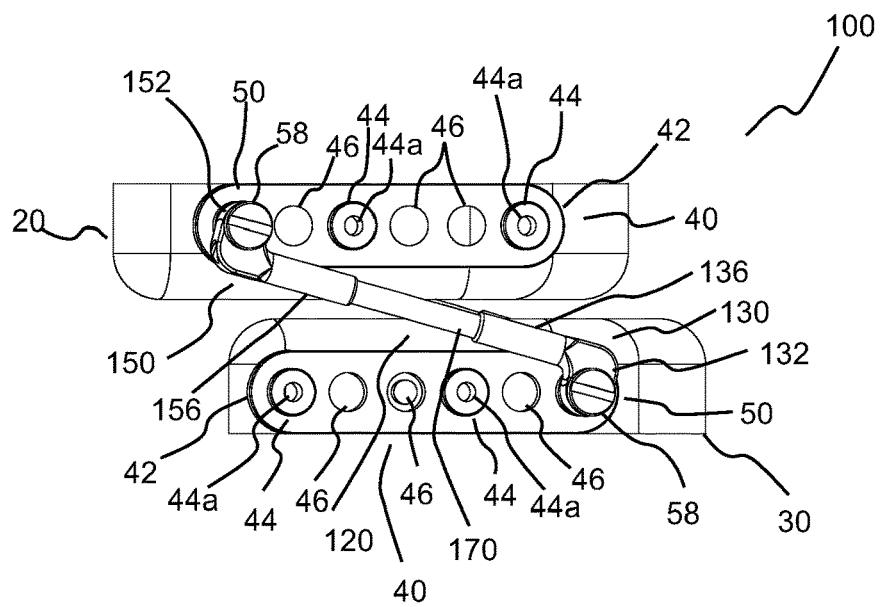
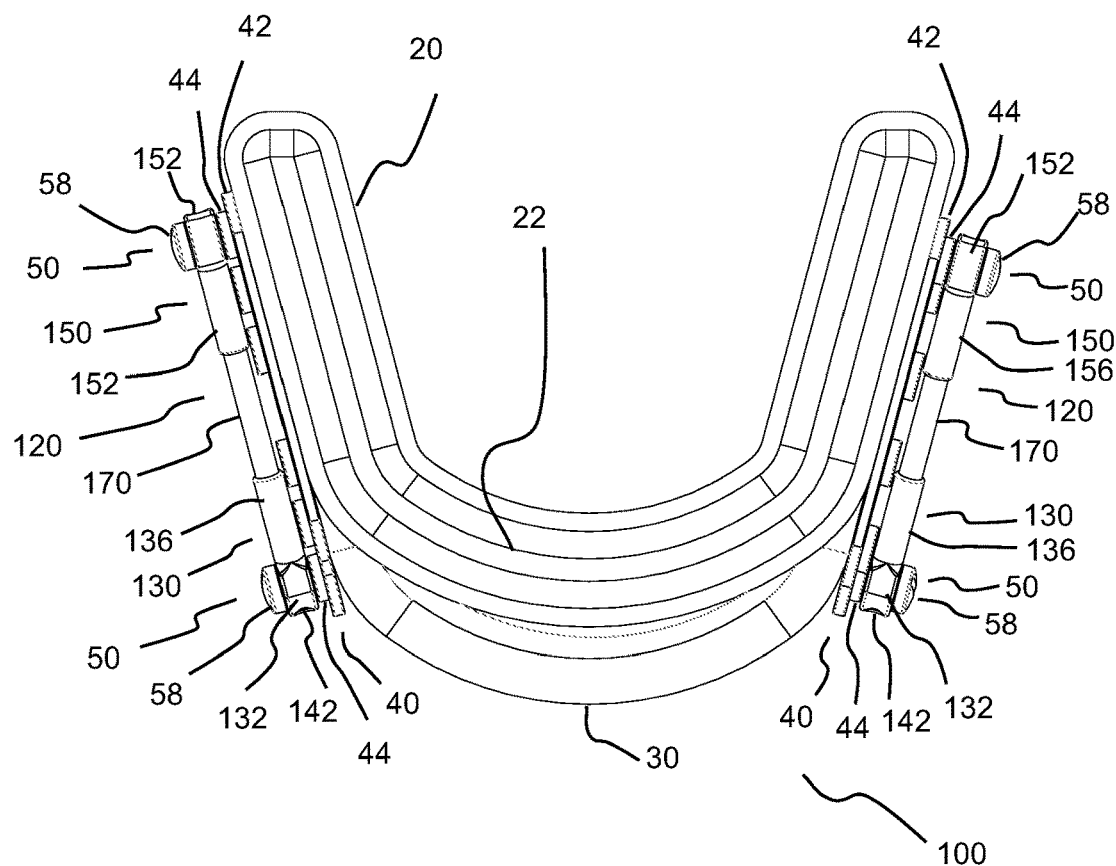
Fig. 2D

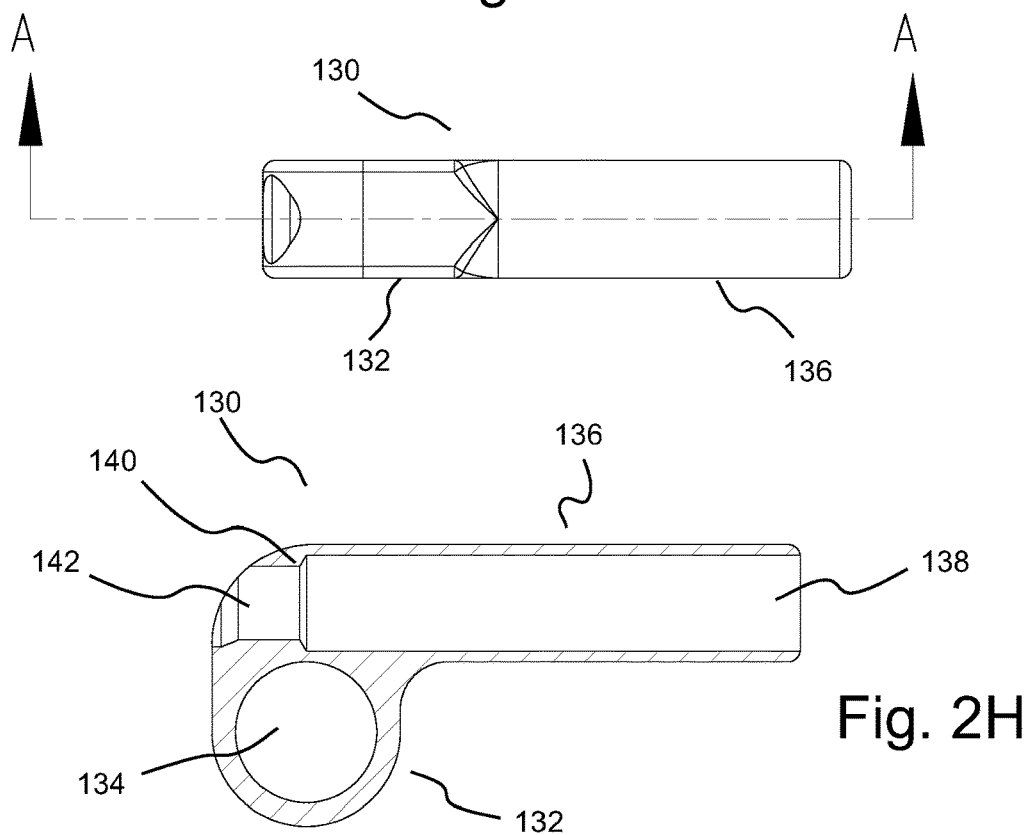
Fig. 2G
Fig. 2H
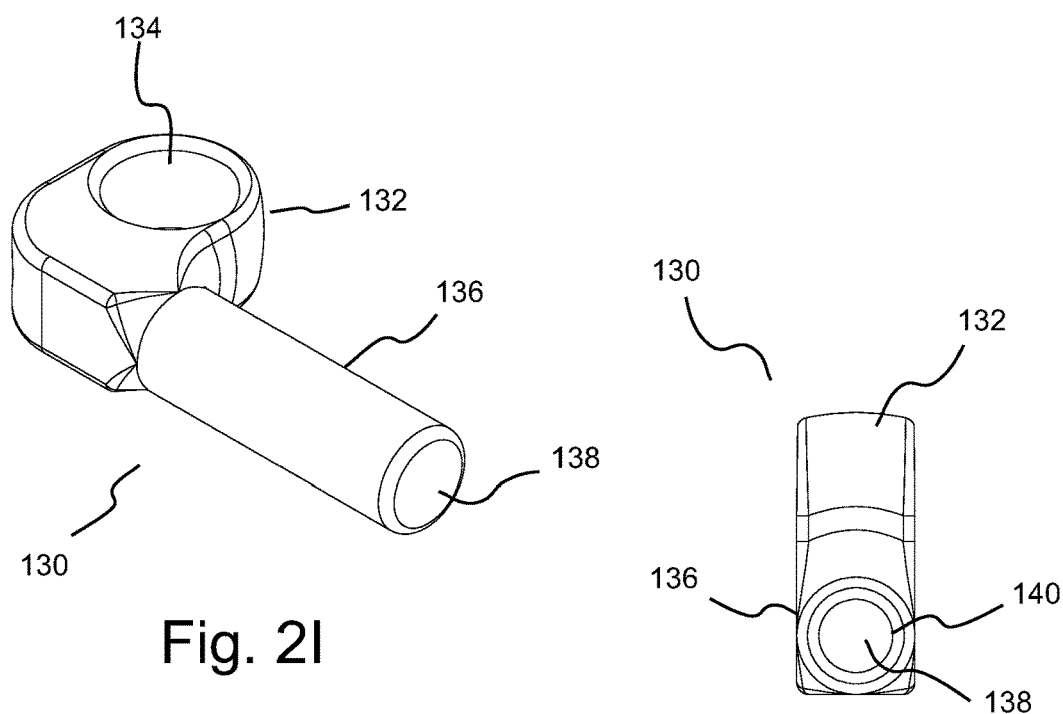
Fig. 2I
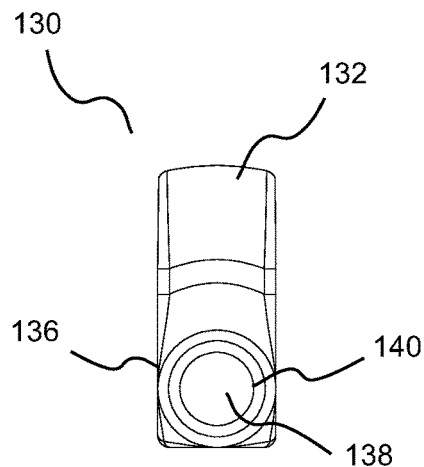
Fig. 2J

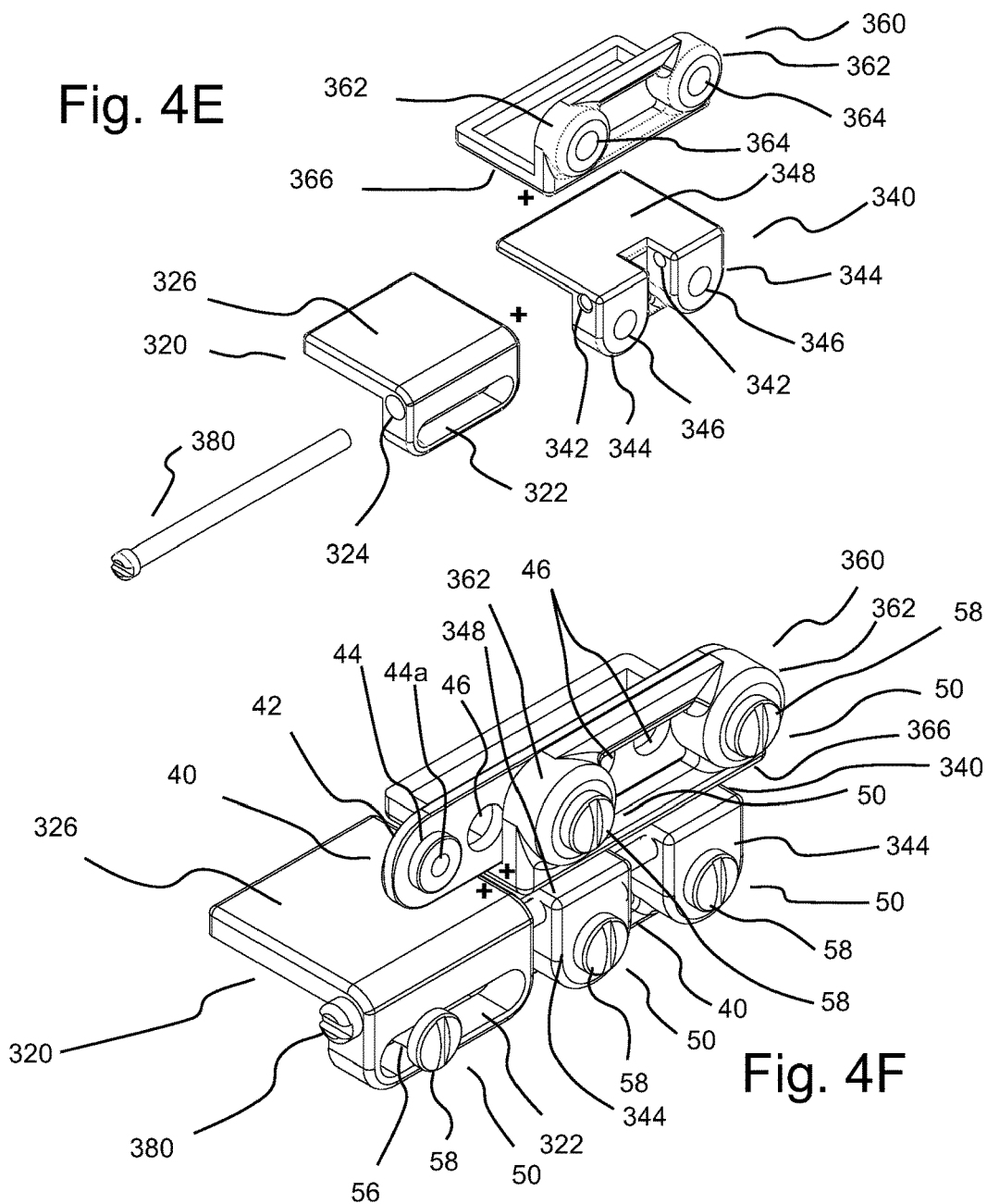
Fig. 4E
Fig. 4F
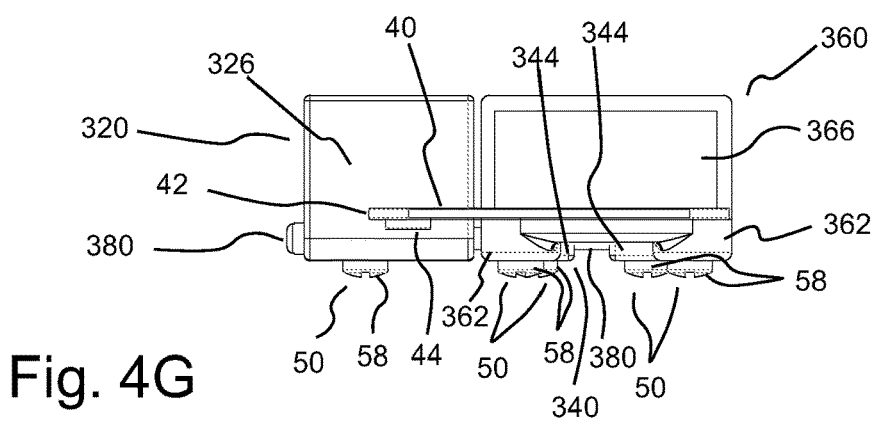
Fig. 4G

Fig. 5A
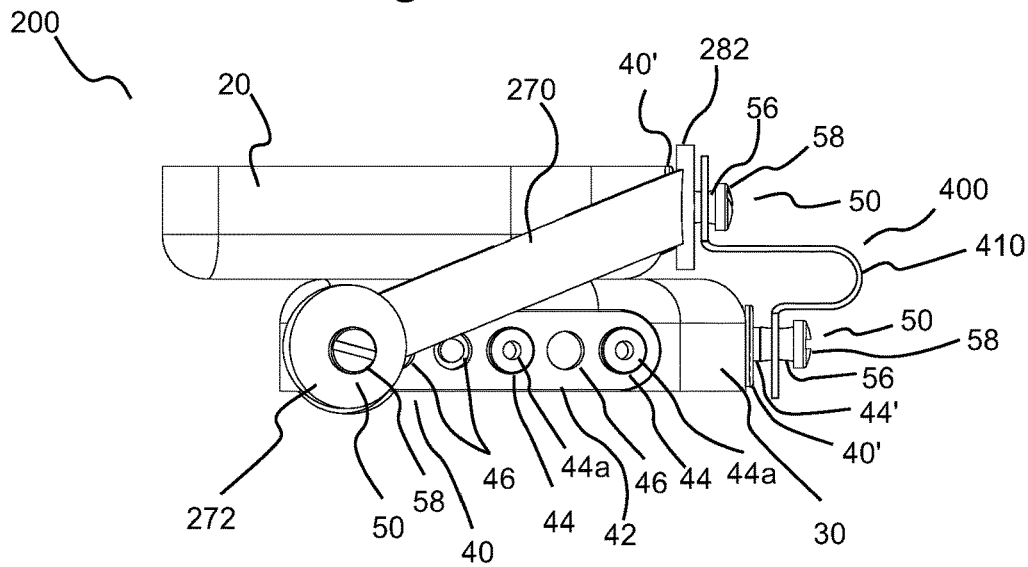
Fig. 5B
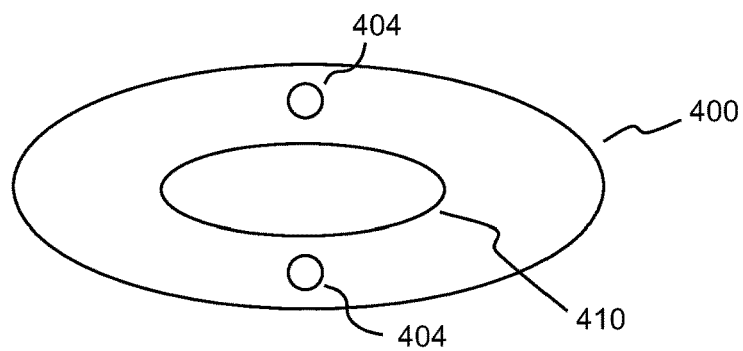
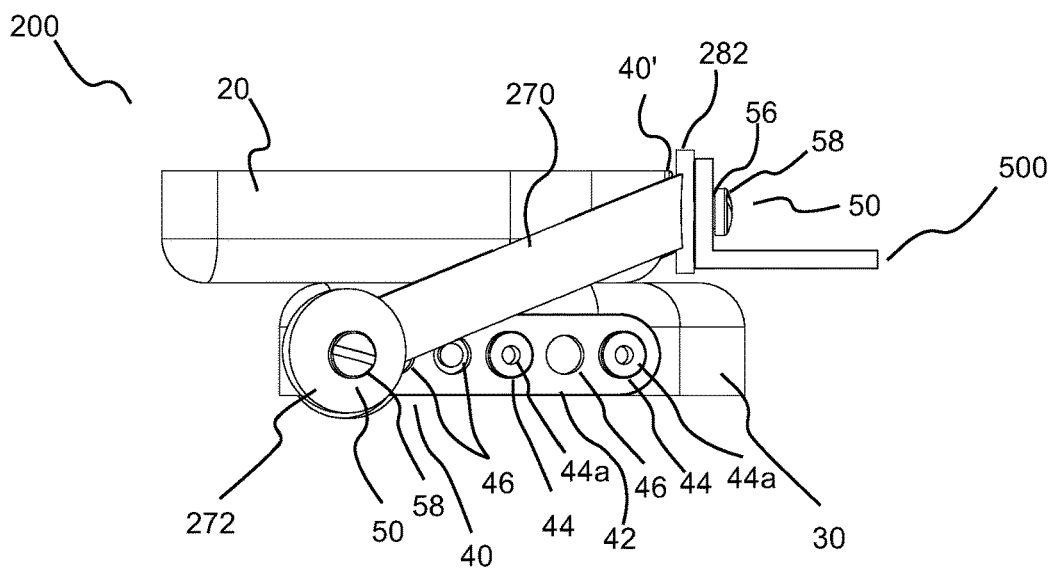
Fig. 6

ORAL ORTHOTIC SYSTEMS, DEVICES AND METHODS FOR USE IN CONNECTION WITH SLEEP-DISORDERED BREATHING

CROSS-REFERENCE TO RELATED APPLICATION

This application is a continuation of U.S. patent application Ser. No. 14/347,800, filed Mar. 27, 2014, which is a 35 U.S.C. 371 National Phase application of International PCT Patent Application number PCT/US2012/058165, filed Sep. 29, 2012, which claims benefit of U.S. Provisional Patent Application Ser. No. 61/541,336, filed Sep. 30, 2011, and U.S. Provisional Patent Application Ser. No. 61/590,600, filed Jan. 25, 2012, the disclosures of which are incorporated herein by reference.

BACKGROUND

The following information is provided to assist the reader in understanding the technologies disclosed below and the environment in which such technologies will typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

There are several types of sleep-disordered breathing including, for example, habitual snoring and obstructive sleep apnea. In obstructive sleep apnea or OSA, as muscle tone in the back of the throat relaxes during sleep, tissue collapses and can obstruct breathing. Symptoms of OSA typically include loud snoring, restless sleep, and daytime sleepiness. Chronic OSA can result in low blood oxygen (hypoxemia), daytime fatigue, memory problems, cardiovascular problems, sleep deprivation of a bed partner and/or other complications.

Continuous positive airway pressure (CPAP) is generally considered a mainstay of treatment for severe obstructive sleep apnea. In some cases, CPAP devices may be poorly tolerated or even rejected because the cumbersome and intrusive nature of the CPAP mask and associated strapping.

Oral orthotic devices are an effective way to control mild to moderate OSA and/or snoring, and are typically found to be less cumbersome than CPAP devices. Moreover, a CPAP mask can be attached to an oral orthotic device for enhanced comfort and stability. Oral orthotic devices for the treatment sleep-disordered breathing are similar to orthodontic appliances. In general, oral orthotic devices for the treatment of sleep-disordered breathing move and stabilize the lower jaw in, for example, a forward position in an effort to create and maintain a patient's upper airway during sleep.

Although a number of oral orthotic devices and/or systems for treatment of sleep-disordered breathing are commercially available, such devices are typically expensive and cumbersome to change to a particular individual's needs. In many cases, if changes are required, a completely new device must be manufactured. If it is determined that a particular type of oral orthotic device is not optimal for use by a particular patient and it is desired to fit the patient with another type of oral orthotic device, a completely new device must be manufactured, resulting in significant delay and expense.

SUMMARY

In one aspect, a method of forming oral orthotic systems to position and/or stabilize a mandible of a patient includes providing an upper dental member adapted to be placed in connection with upper dentition of the patient, providing a lower dental member adapted to be placed in connection with lower dentition of the patient and providing a plurality of posterior mounting structures. Each of the posterior mounting structure is adapted to be attached to one of the upper dental member or the lower dental member at a posterior, buccal position thereon. Each of the posterior mounting structures includes an extending member which includes a plurality of positions at which one of a plurality of connectors is attachable to the extending member. Force may be applied to the mandible of the patient via at least one of a plurality of different mechanisms via attachment of a component of the mechanism to at least one of the posterior mounting structures. The upper dental member and the lower dental member may, for example, be formed, independently, from a polymeric material, a ceramic material, a composite material or the like.

In a number of embodiments, each of the posterior mounting structures is formed in substantially the same manner. Each of the posterior mounting structures may, for example, include a plurality of connector seatings to which one of the plurality of connectors is attachable. Each of the plurality of connector seatings may, for example, include a threaded passage to cooperate with a threaded section of a shaft of one of the plurality of connectors. In a number of embodiments, the shaft of each of the plurality of connectors further includes a non-threaded section attached to the threaded section and a radially extending flange attached to the non-threaded section.

The method may further include attaching one of the plurality of posterior mounting structures to the lower dental member at a posterior, buccal position on a first side thereof and attaching one of the plurality of posterior mounting structures to the lower dental member at a posterior, buccal position on a second side thereof.

In a number of embodiments, the method further includes attaching one of the plurality of posterior mounting structures to the upper dental member at a posterior, buccal position on a first side thereof and attaching one of the plurality of posterior mounting structures to the upper member at a posterior, buccal position on a second side thereof.

In a number of embodiments, the method may further include attaching a first end of a first rod (or extending rigid member) assembly to the posterior mounting structure on the first side of the upper dental member via at least one of the connectors and attaching a second end of the first rod assembly to the posterior mounting structure on the first side of the lower dental member via at least one of the connectors. The method may further include attaching a first end of a second rod assembly to the posterior mounting structure on the second side of the upper dental member via at least one of the connectors and attaching a second end of the second rod assembly to the posterior mounting structure on the second side of the lower dental member via at least one of the connectors. The length of the first rod assembly and the length of the second rod assembly are adapted to apply a forward force to the mandible. The length of the first rod assembly may be adjustable, and the length of the second rod assembly may be adjustable.

In a number of embodiments, the method may further include attaching a first lower mount member to the posterior mounting structure on the first side of the lower dental member via at least one of the connectors and attaching another first lower mount member to the posterior mounting structure on the second side of the lower dental member via at least one of the connectors. Each of the first lower mount members includes at least one magnetic section. In such embodiments, the method may further include attaching a first upper mount member to the posterior mounting structure on the first side of the upper dental member via at least one of the connectors and attaching another first upper mount member to the posterior mounting structure on the second side of the upper dental member via at least one of the connectors. Each of the first upper mount members includes at least one magnetic section. The polarities of the magnetic sections of the first upper mount members and the magnetic sections of the first lower mount members are arranged to apply a forward force to the mandible.

The position of each of the first lower mount members on the posterior mounting structure to which it is attached may, for example, be adjustable. In a number of embodiments, each of the first lower mount members comprises an extending slot via which each the at least one of the connectors passes.

The method may further include attaching a second lower mount member to the posterior mounting structure on the first side of the lower dental member via at least one of the connectors posterior to the first lower mount member on the first side of the lower dental member. The first lower mount member on the first side of the lower dental member may be movably connected to the second lower mount member on the first side of the lower dental member via an adjustable connector. Similarly, the method may further include attaching a second lower mount member to the posterior mounting structure on the second side of the lower dental member via at least one of the connectors posterior to the first lower mount member on the second side of the lower dental member. The first lower mount member on the second side of the lower dental member may be movably connected to the second lower mount member on the second side of the lower dental member via an adjustable connector.

An upper section of the second lower mount member on the first side of the lower dental member may, for example, be adapted to contact a lower section of the first upper mount member on the first side of the upper dental member. Likewise, an upper section of the second lower mount member on the second side of the lower dental member may be adapted to contact a lower section of the first upper mount member on the second side of the upper dental member. Such contact may, for example, be used to maintain a predetermined distance between a patients upper teeth/dentition and lower teeth/dentition.

The upper section of the second lower mount member on the first side of the lower dental member may, for example, be magnetically attracted by the magnetic section of the first upper mount member on the first side of the upper dental member, and the upper section of the second lower mount member on the second side of the lower dental member may, for example, be magnetically attracted by the magnetic section of the first upper mount member on the second side of the upper dental member. Upper and lower mount members may, for example, be used to maintain a predetermined distance between a patient's upper and lower dentition in generally any embodiment hereof.

In a number of embodiments, the method may include attaching a extending rigid link to a first, buccal side of the lower dental member at a first end of the extending rigid link and attaching the rigid link to a first, buccal side of the lower dental member at a second end of the extending rigid link. The extending rigid link is adapted to prevent posterior movement of a lower jaw of the patient relative to an upper jaw of the patient beyond a determined range. The extending rigid link includes a first connecting section at a first end thereof that is snapped over the a connector attached to the first buccal sided of the upper dental member and a second connecting section at a second end that is snapped over another connector attached to the first buccal side of the lower dental member. The method may further include attaching another extending rigid link to a second, buccal side of the lower dental member at a first end of the another extending rigid link and attaching the another rigid link to a second, buccal side of the lower dental member at a second end of the another extending rigid link. The another extending rigid link includes a first connecting section at a first end thereof that is snapped over a connector attached to the second buccal side of the upper dental member and a second connecting section at a second end that is snapped over another connector attached to the second buccal side of the lower dental member.

In a number of embodiments, the method further includes attaching least one sloped upper abutment member in operative connection with the upper dental member via at least one of the connectors and attaching at least a one sloped lower abutment member in operative connection with the lower dental member via one of the connectors to make abutting contact with the at least one sloped upper abutment member. Abutment of the at least a one sloped lower abutment member with the at least a one sloped upper abutment member causes an increase in an opening between the upper dental member and the lower dental member as the lower dental member is moved forward relative to the upper dental member.

In a number of embodiments, the method further includes attaching an anterior mounting structure to the upper dental member at an anterior position thereon. The method may further include connecting at least one elastomeric member to the anterior mounting structure via at least one of the connectors and connecting the elastomeric member to posterior mounting structure on the first side of the lower dental member so that the elastomeric member applies a forward force to the mandible. The elastomeric member may, for example, also be attached to posterior mounting structure on the second side of the lower dental member.

The method may further include attaching a component such as a titration system, a lip seal system, a tongue retention system and/or a mask of a PAP/CPAP device or system to one or both of the upper dental member and the lower dental member. Such components may, for example, be attached via an anterior mounting structure attached at an anterior position on the upper dental member and/or at an anterior position on the lower dental member.

In another aspect, a system for forming oral orthotic systems to position a mandible of a patient includes an upper dental member adapted to be placed in connection with upper dentition of the patient, a lower dental member adapted to be placed in connection with lower dentition of the patient, a plurality of connectors; and a plurality of like posterior mounting structures. Each of the posterior mounting structures is adapted to be attached to one of the upper dental member or the lower dental member at a posterior, buccal position thereon. Each of the posterior mounting structures includes an extending member which includes a plurality of positions at which one of the plurality of connectors is attachable to the extending member. Force may be applied to the mandible of the patient via at least one of a plurality of different mechanisms via attachment of a component of the mechanism to at least one of the posterior mounting structures.

In another aspect, an oral orthotic system to position and/or stabilize a mandible of a patient includes an upper dental member adapted to be placed in connection with upper dentition of the patient, a lower dental member adapted to be placed in connection with lower dentition of the patient, an extending elastomeric member adapted to be attached to a first, buccal side of the lower dental member at a first end of the extending elastomeric member, and to be attached to a second, buccal side of the lower dental member at a second end of the extending elastomeric member. The extending elastomeric member is further adapted to be operatively connected to an anterior position on the upper dental form at a position on the extending elastomeric member intermediate between the first end and the second end.

In a number of embodiments, the lower dental member includes a first connector extending outwardly on the first, buccal side of the lower dental member and a second connector extending outwardly the second, buccal side of the lower dental member. The first end of the extending elastomeric member may, for example, include a passage or other cooperating connector adapted to connect to the first connector. The second end of the extending elastomeric member may, for example, include a passage or other cooperating connector adapted to connect to the second connector. In a number of embodiments, the upper dental member includes a third connector at an anterior position thereon extending forward, and the extending elastomeric member may, for example, include a third passage or other cooperating connector adapted to connect to the third connector.

In another aspect, an oral orthotic system to position a mandible of a patient includes an upper dental member adapted to be placed in connection with upper dentition of the patient and a lower dental member adapted to be placed in connection with lower dentition of the patient. At least one connector is attached to a first buccal side of the upper dental member, wherein the connector includes a radially extending flange or head. At least one connector is also attached to the first buccal side of the lower dental member, wherein the connector includes a radially extending flange or head. The oral orthotic system further includes an extending rigid link adapted to be attached to the first, buccal side of the upper dental member at a first end of the extending rigid link and to be attached to the first buccal side of the lower dental member at a second end of the extending rigid link. The extending rigid link is adapted to prevent posterior movement of a lower jaw of the patient relative to an upper jaw of the patient beyond a determined range. The extending rigid link includes a first connecting section at a first end thereof adapted to snap over the at least one connector attached to the first buccal side of the upper dental member and a second connecting section at a second end thereof adapted to snap over the at least one connector attached to the first buccal side of the lower dental member.

In a number of embodiments, the extending rigid link includes a first extending member attached to a first side of the first connecting section at a first end of the first extending member and to a first side of the second connection section at a second end of the first extending member. The extending rigid link may further include at least a second extending member attached to a second side of the first connecting section at a first end of the second extending member and to a second side of the second connection section at a second end of the first extending member. The rigid link may, for example, be formed generally in the form of a loop.

In a further aspect, an oral orthotic system to position a mandible of a patient includes an upper dental member adapted to be placed in connection with upper dentition of the patient, a lower dental member adapted to be placed in connection with lower dentition of the patient, at least one sloped upper abutment member in operative connection with the upper dental member and at least a one sloped lower abutment member in operative connection with the lower dental member to make abutting contact with the at least one sloped upper abutment member. Abutment of the at least a one sloped lower abutment member with the at least a one sloped upper abutment member causes an increase in an opening between the upper dental member and the lower dental member as the lower dental member is moved forward relative to the upper dental member.

A number of advantages are provided by the devices, systems and/or methods hereof. For example, the devices, systems and/or methods hereof create effective mandibular repositioning/stabilization, while enabling variations in the manner of mandibular repositioning/stabilization without having to completely create or re-create several different oral appliances. This enables, for example, a dentist to render care more quickly, more efficiently, more physically effectively, and more cost effectively.

During a first visit or initial consultation, a patient may, for example, be offered several variations for oral orthotic systems adapted to conform to the patient's emotional, psychological and clinical needs. In the systems hereof, there is no need for the caregiver to make an "educated guess" as to an appropriate oral orthotic system, only to have to subsequently change to a different system design, which must be completely remanufactured to unique specifications.

Once an initial consultation has occurred and a system type is determined, at a subsequent appointment, the caregiver may deliver an initial system hereof to the patient as a "good starting point." If design changes are required, the system can be quickly, easily, and inexpensively changed depending upon patient feedback or clinical observation. The systems hereof can be interchanged from one type of application to another within, for example, 10 to 15 minutes, without the delay and expense of outside laboratory procedures. Such changes may be spurred by patient feedback regarding, for example, claustrophobia (merinthophobia; fear of being bound), temporomandibular joint sensitivity, tooth sensitivity, tooth mobility, patient preferences and/or clinical effectiveness.

Applying force to the mandible of the patient via different mechanisms (the interchangeability of which is facilitated in the devices, systems and/or methods hereof) results in different "feels" to the patient. For example, using one or more elastomeric members provides a "pulling" force on the lower jaw or mandible, wherein a forward position or positions on the upper jaw act as an anchor in pulling the mandible forward from a rearward or posterior connection to the lower jaw or mandible. A system including one or more rigid member such as a rod assembly provides a "pushing" force on the lower jaw. Such a system, uses an upper jaw, rearward anchor to push the lower jaw forward by virtue of a rigid connection to the front part of the lower jaw. A magnetic system can provide either a pulling force or a pushing force depending upon the arrangement of the poles of the magnetic sections thereof.

Moreover, one may readily and quickly alter the vertical dimension, the distance between the upper and lower teeth or the bite opening readily and quickly in any of the various system variations hereof adding cooperating or contacting mount member to the upper dental members and lower dental members hereof. Adjusting the distance between the upper and lower teeth of the patient may, for example, result in improved feel and effectiveness.

Furthermore, add-on components are readily and quickly added to the systems hereof as needed (for example, such add-on components may include a sleep lab titration/adjustment system, a tongue retaining system, a lip seal system, and/or a PAP/CPAP mask). Such add-on components positively impact effectiveness in a relatively ready, quick and inexpensive manner.

The devices, systems and methods hereof, along with the attributes and attendant advantages thereof, will best be appreciated and understood in view of the following detailed description taken in conjunction with the accompanying drawings.

BRIEF DESCRIPTION OF THE DRAWINGS

FIG. 1B illustrates a perspective view of a rearward or posterior mounting of the subassembly of FIG. 1A.

FIG. 1C illustrates a bottom view of the mounting structure of FIG. 1A with an embodiment of a connector is aligned for attachment thereto.

FIG. 2C illustrates a side view of the system of FIG. 2A.
FIG. 2D illustrates a top view of the system of FIG. 2A.

FIG. 2G illustrates a top view of a first member of the rod assembly of FIG. 2F for pivotal attachment of the rod assembly to the lower dental member of the system of FIG. 2A.

FIG. 2H illustrates a cross-sectional view of the first member of the rod assembly of FIG. 2F along section A-A of FIG. 2G.

FIG. 2I illustrates a perspective view of the first member of the rod assembly of FIG. 2F.

FIG. 2J illustrates a front view of the first member of the rod assembly of FIG. 2F.

FIG. 4E illustrates a perspective, exploded view of a subassembly or subsystem of the system of FIG. 4A through which magnetic force applies a forward force to the mandible.

FIG. 4F illustrates a perspective view of the subassembly or subsystem of FIG. 4E in an assembled state, attached to upper and lower mounting structures of the system of FIG. 4A.

FIG. 4G illustrates a top view of the subassembly or subsystem of FIG. 4E in an assembled state, attached to upper and lower mounting structures of the system of FIG. 4A.

FIG. 5A illustrates a side view of the system of claim 3A with an embodiment of a lip seal attached thereto.

FIG. 5B illustrates a front view of the lip seal of FIG. 5A.

FIG. 6 illustrates a side view of the system of FIG. 3A wherein a device is attached to an anterior mounting structure of the upper dental member thereof.

DETAILED DESCRIPTION OF THE INVENTION

As used herein and in the appended claims, the singular forms "a," "an", and "the" include plural references unless the context clearly dictates otherwise. Thus, for example, reference to "a connector" includes a plurality of such connectors and equivalents thereof known to those skilled in the art, and so forth, and reference to "the connector" is a reference to one or more such connectors and equivalents thereof known to those skilled in the art, and so forth.

Figure 1A:
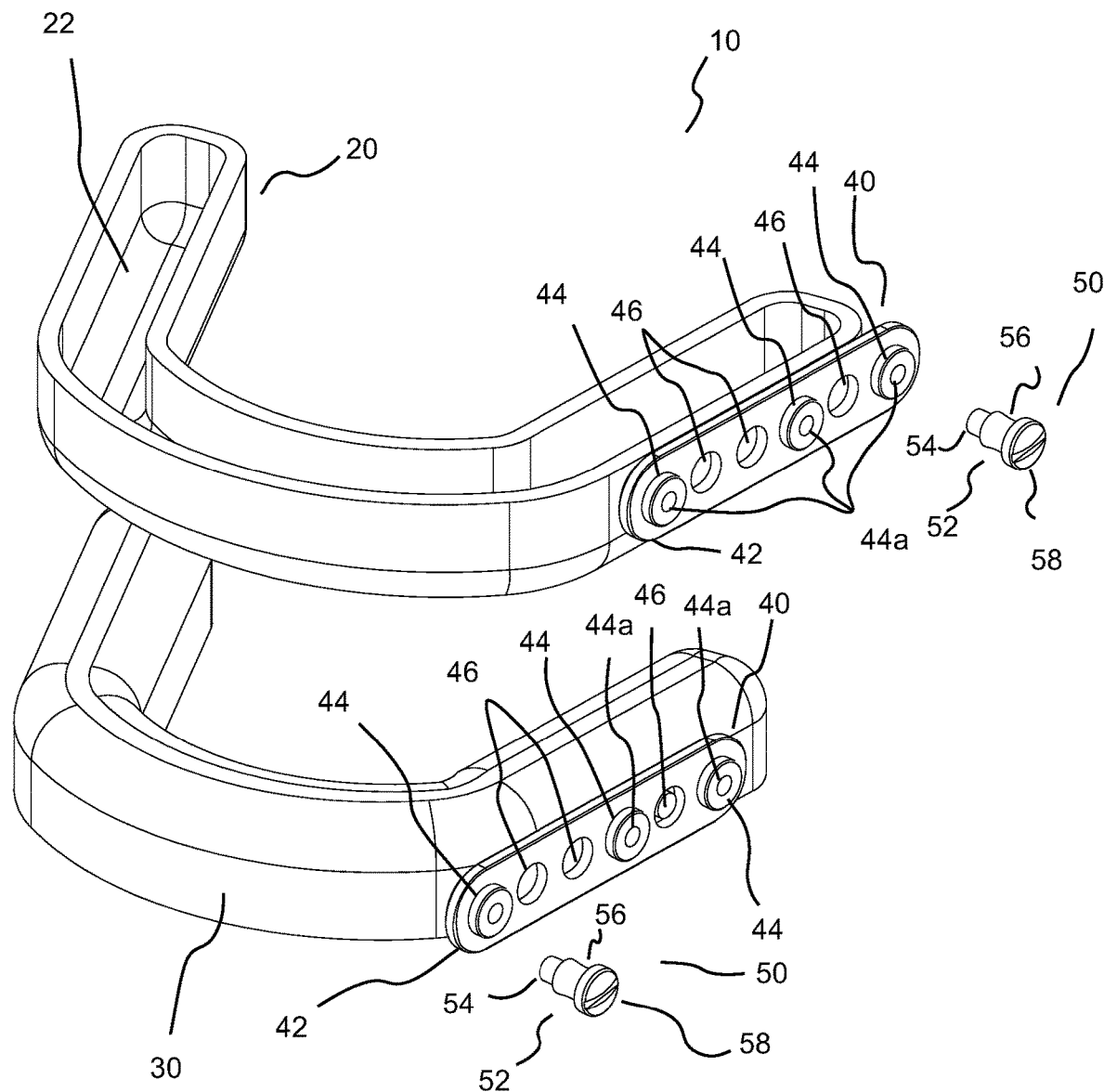
FIG. 1A illustrates a perspective, partially exploded view of an embodiment of a subassembly, subsystem or system for use in one or more oral orthotic systems hereof.

FIGS. 1A through 1C illustrate an embodiment of a subassembly, subsystem or system 10 (see FIG. 1A) hereof, all or part of which can be used in connection with forming a number of types of oral orthotic systems for use in connection with sleep-disordered breathing. A number of such oral orthotic system are describe herein. However, one skilled in the art appreciates that other oral orthotic system may be formed using "universal" system 10. System 10 includes an upper or maxillary dental tray, base or member 20 and a lower or mandibular dental tray, base or member 30. As known in the art, in forming upper dental member 20 and lower dental member 30, impressions are first taken of an individual's dentition to form casts, and a polymeric material (for example, an acrylic material) is used to cast upper dental member 20 and lower dental member 30. Upper dental member 20 thus includes a cavity or seating 22 which is formed to and receives the individual's upper teeth. Lower dental member 30 includes a similar cavity or seating (not shown in FIGS. 1A through 1C) which is formed to and receives the individual's lower teeth. For ease of representation, upper dental member 20 and lower dental member 30 are illustrated generically and the forms of the individual's dentition are not shown in the Figures.

System 10 further includes a plurality of posterior (or rearward) mounting structures 40. In the illustrated embodiment, each posterior mounting structure 40 includes an extending element or member 42. Extending member 42 may, for example, be formed to be generally linear or may be curved over at least a portion thereof. In the illustrated embodiment, extending member 42 was formed to be linear. In a number of embodiments, mounting structures were formed from a metal such as stainless steel or any other biocompatible metal. A plurality of connector seatings 44 (three in the illustrated embodiment) are positioned at spaced positions along the length of extending member 42. In the illustrated embodiment, connector seatings 44 include passages 44a, which may, for example, be threaded. In the illustrated embodiment, three connector seatings 44 of extending members 42 are not evenly spaced on extending member 42. As, for example, illustrated in FIG. 1B the connector seating 44 on the right side of extending member 40 (in the orientation illustrated in FIG. 1B) is closer to the intermediate mounting connector than is the mounting connector 44 on the left side thereof. A clear to those skilled in the art, differing numbers, types and arrangements or connector seatings thereof are possible.

In forming the oral orthotic systems hereof, extending members 42 may, for example, be embedded within a polymeric material of upper dental member 20 and lower dental member 30 during the formation thereof. In several embodiments, upper dental member 20 and a lower dental member 30 were formed in a two-step process wherein upper dental member 20 and lower dental member 30 were first cast to include impressions of the individual's dentition using a first polymeric material as described above. Subsequently, posterior mounting structures 40 and/or one or more anterior mounting structures 40' (described further below) were attached thereto by positioning the mounting structure at the desired position and adding a second polymeric material to embed the mounting structure in the second polymeric material. The first polymeric material and the second polymeric material may be the same or different and are suitably compatible to form a suitable bond therebetween. In a number of embodiments, the first polymeric material was a first acrylic polymer, and the second polymeric material was a second, different acrylic polymer. In the figures, upper dental member 20 and lower dental member 30 are illustrated before the embedding process with the second polymeric material. Mounting structure hereof may alternatively be attached to upper dental member 20 and/or a lower dental member 30 in a single-step, polymeric casting or molding process. As also clear to those skilled in the art, the attached posterior and anterior mounting structures hereof may be formed monolithically with upper dental member 20 and/or lower dental member 30, which may, for example, be formed from a material (for example, a polymeric material, a ceramic material, or a composite material) of suitable properties to support connectors 50 described further below.

In embodiments wherein the posterior mounting structures 40 are formed separately from the remaining portions of upper dental member 20 and lower dental member 30, extending members 42 may, for example, include one or more features that enhance the structural bond or connection between the polymeric material and extending members 42. In the illustrated embodiments, extending members 42 include a number of openings or passages 46 into which polymeric material flows during molding to enhance the structural bond or connection of extending members 42 with the polymeric material of upper dental member 20 and lower dental member 30. In a number of embodiments, extending members 42 were positioned within the polymeric materials of upper dental member 20 and lower dental member 30 such that the openings of passages 44a were generally flush or coplanar with the outer, gum or buccal sides of upper dental member 20 and lower dental member 30.

Connectors 50 cooperate with connector seatings 44. In the illustrated embodiment, connectors 50 include an extending shaft 52 having a threaded portion 54 (see FIG. 1B) on an inner section thereof. Threaded portion 54 cooperates with threading on an interior wall of passages 44a to secure mounting connectors 50 to extending members 42 of posterior mounting structures 40. A section of shaft 56, positioned outside of threaded portion 54 is not threaded in the illustrated embodiment. A radially outward (with respect to the axis of extending shaft 52) extending flange or head 58 of mounting connectors 50 is connected to an outer end of shaft 52.

In the embodiment of system 10 illustrated in FIG. 1A, posterior mounting structures 40 formed within or embedded within upper dental member 20 and lower dental member 30 are substantially identical or formed to be of like kind. For example, each mounting structure 40 may include the same number of connector seatings 44 and/or the positions of each of the plurality of connector seatings 44 on each mounting structure may have generally the same relative spacings therebetween. Posterior mounting structures 40, may, for example, be generally symmetrical about a center line C (see FIG. 1B) for use on either side of either upper dental member 20 and lower dental member 30. Posterior mounting structures 40 and connectors 50 may be used "universally" in connection with a number of embodiments of oral orthotic devices or devices. As will be described further below, one or more additional mounting structures of a different type can be used in various embodiments of oral orthotic devices hereof.

Figure 2A:
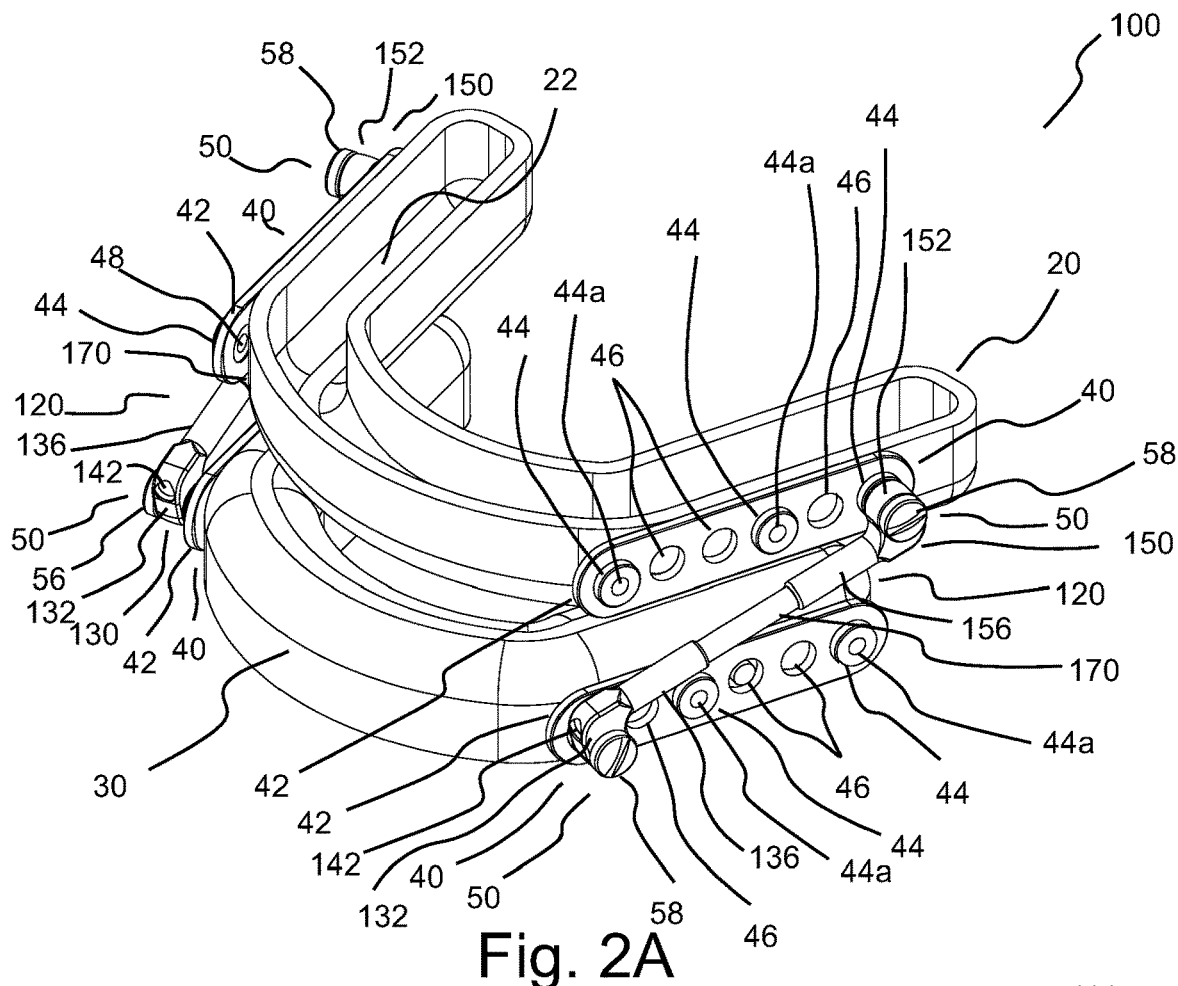
FIG. 2A illustrates an upper, perspective view of an embodiment of an oral orthotic system for treatment of sleep-disordered breathing.
Figure 2B:
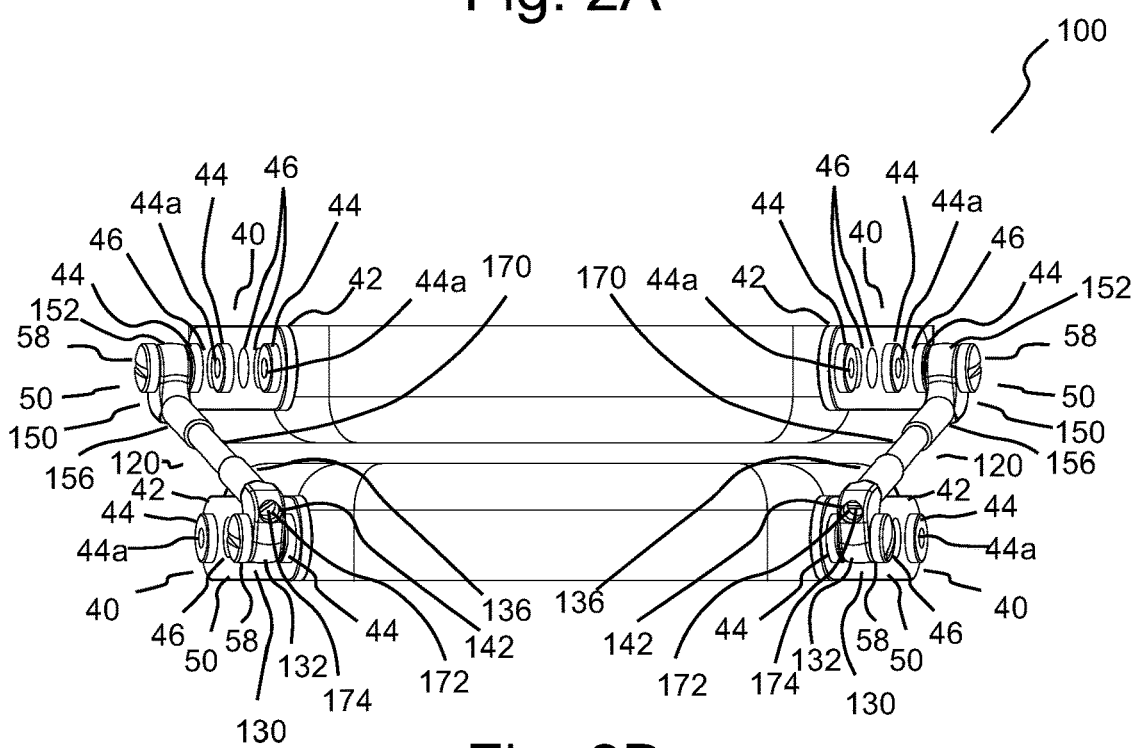
FIG. 2B illustrates a front view of the system of FIG. 2A.
Figure 2E:
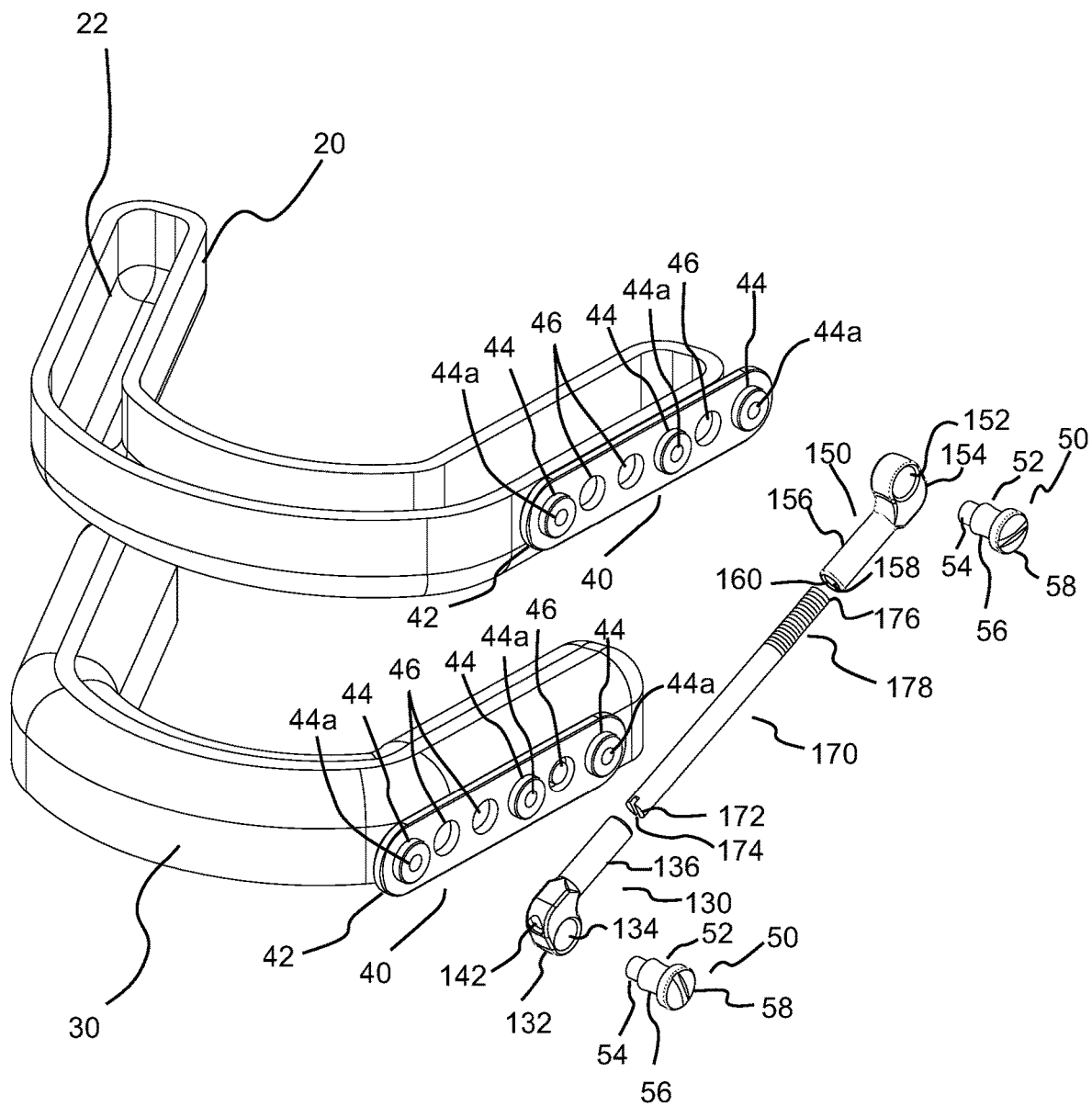
FIG. 2E illustrates a perspective exploded view of the system of FIG. 2A.
Figure 2F:
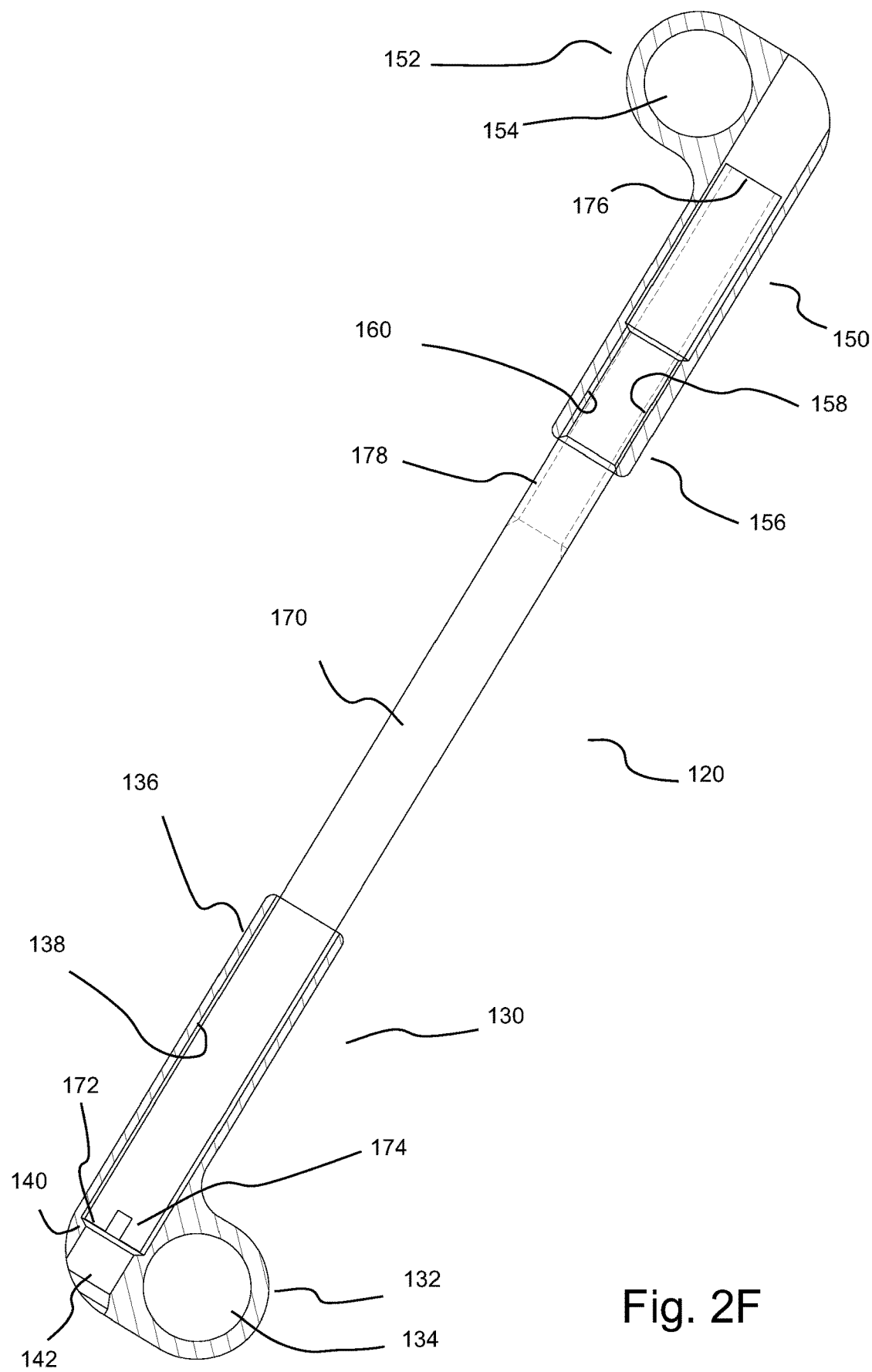
FIG. 2F illustrates cross-sectional view of an extending connector system or rod assembly of the system of FIG. 2A.
Figure 2K:
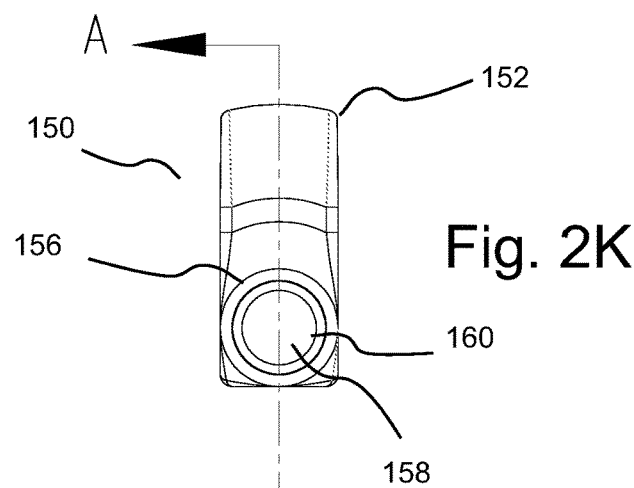
FIG. 2K illustrates a front view of a second member of the rod assembly of FIG. 2F for pivotal attachment of the rod assembly to the upper dental member of the system of FIG. 2A.
Figure 2L:
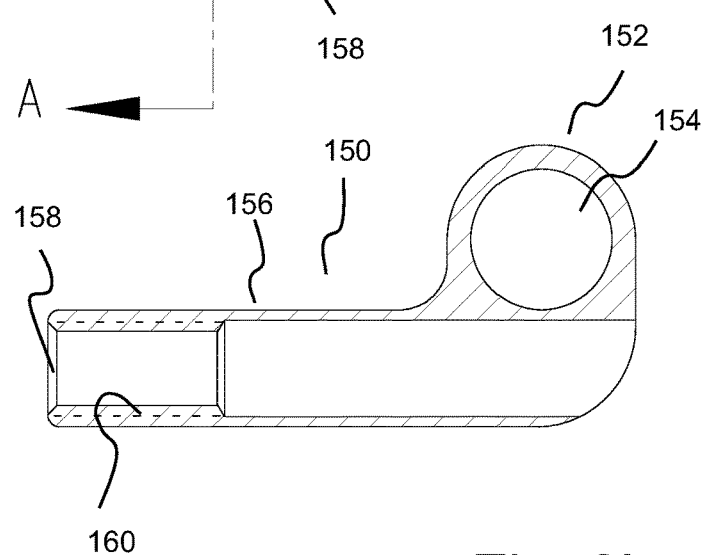
FIG. 2L illustrates a cross-sectional view of the second member of the rod assembly of FIG. 2F along section A-A of FIG. 2K.
Figure 2M:
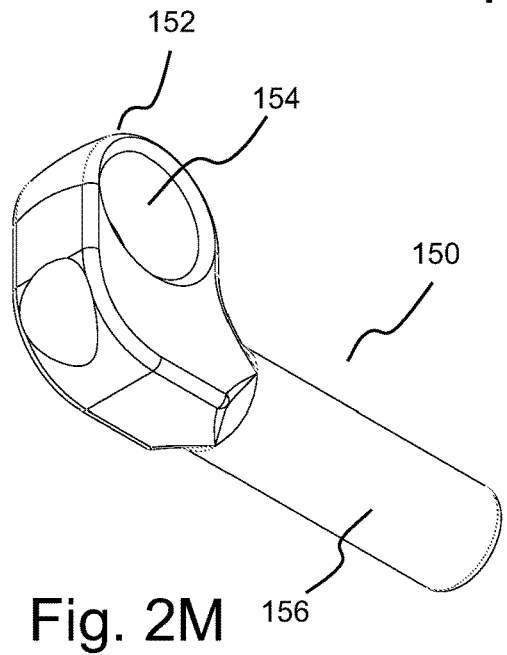
FIG. 2M illustrates a perspective view of the second member of the rod assembly of FIG. 2F.
Figure 2N:
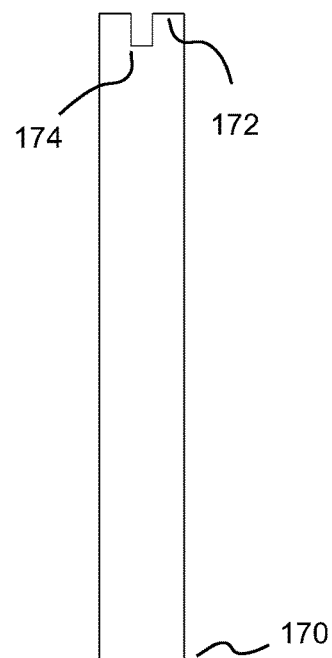
FIG. 2N illustrates a side view of the rod member or intermediate extending member of the rod assembly of FIG. 2F.
Figure 3A:
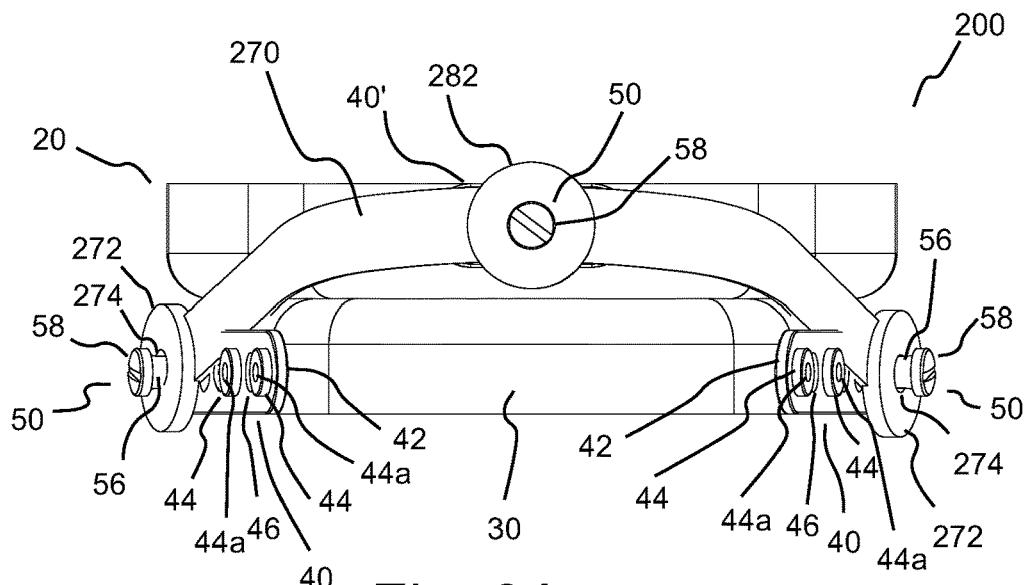
FIG. 3A illustrates a front view of another embodiment of an oral orthotic system for treatment of sleep-disordered breathing.
Figure 3B:
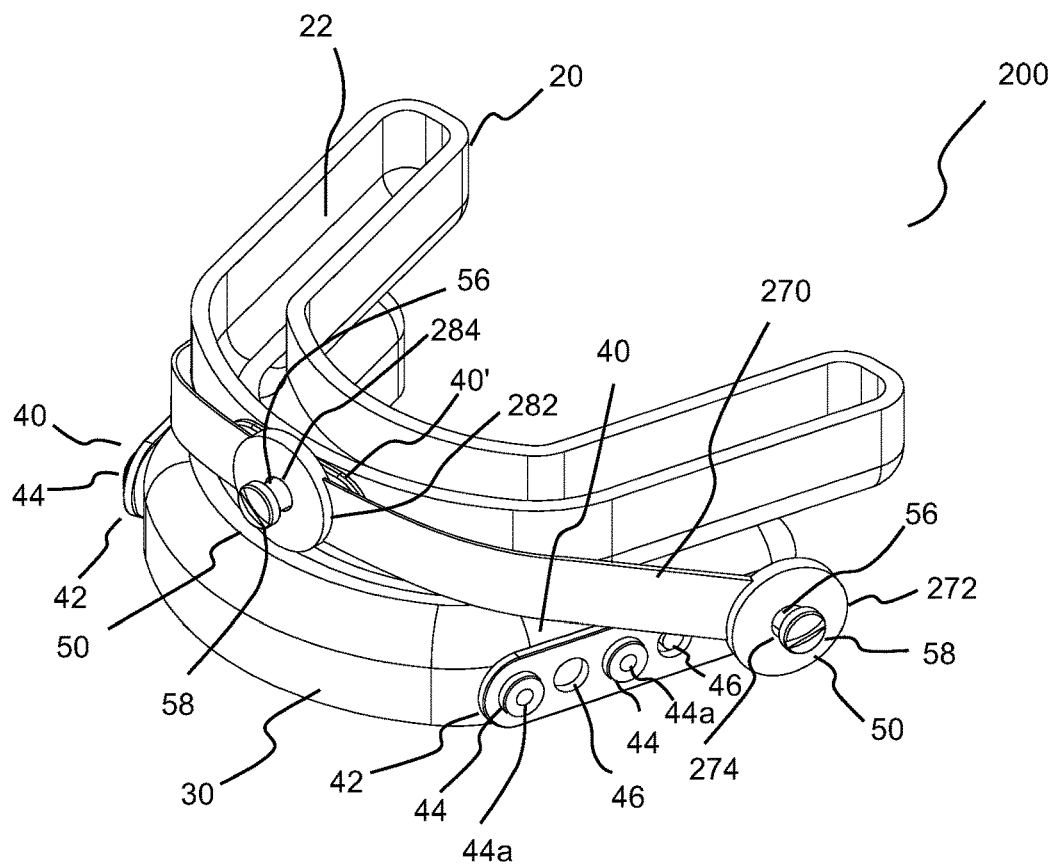
FIG. 3B illustrates an upper, perspective view of the system of FIG. 3A.
Figure 3C:
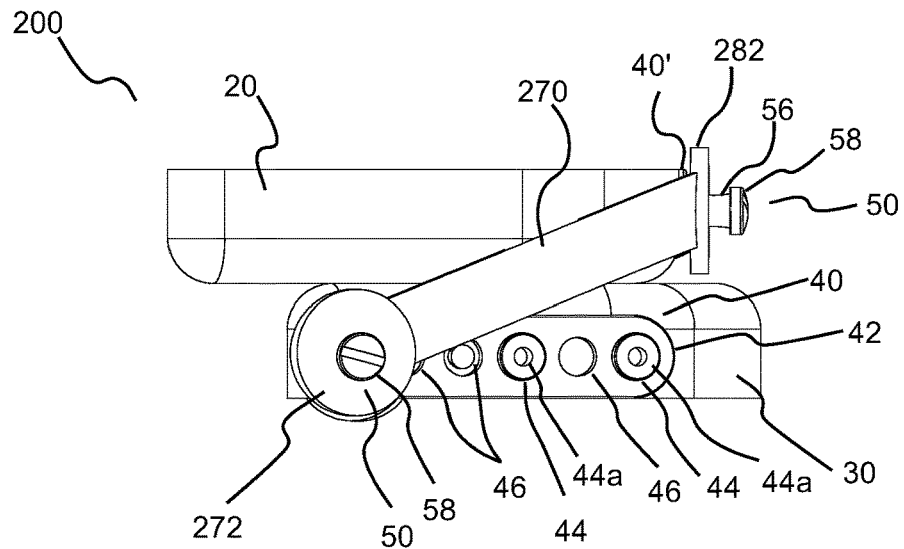
FIG. 3C illustrates a side view of the system of FIG. 3A.
Figure 3D:
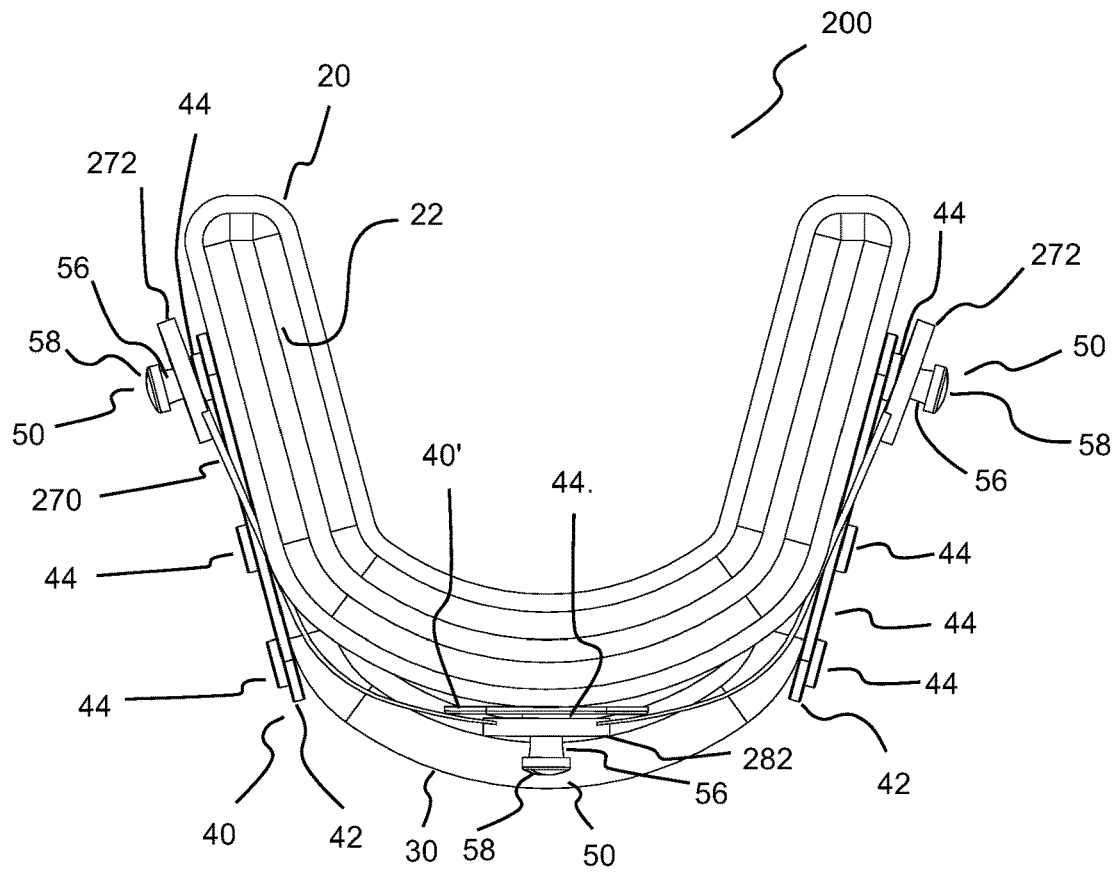
FIG. 3D illustrates a top view of the system of FIG. 3A.
Figure 3E:
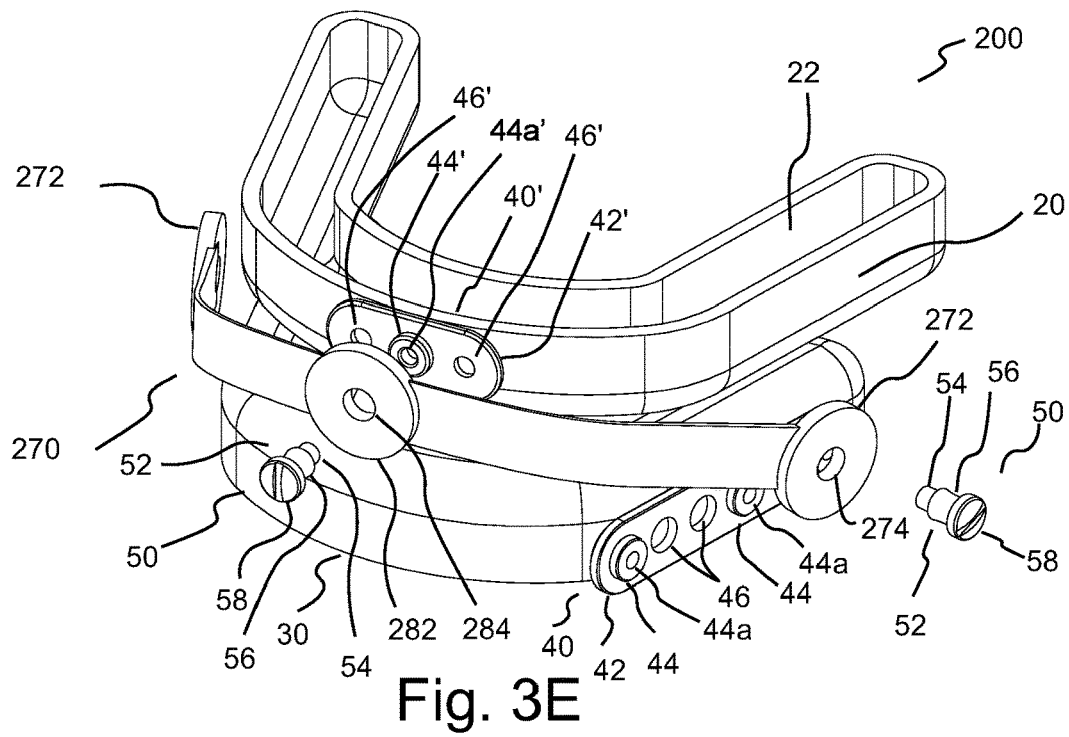
FIG. 3E illustrates a perspective exploded view of the upper the system of FIG. 3A.
Figure 3F:
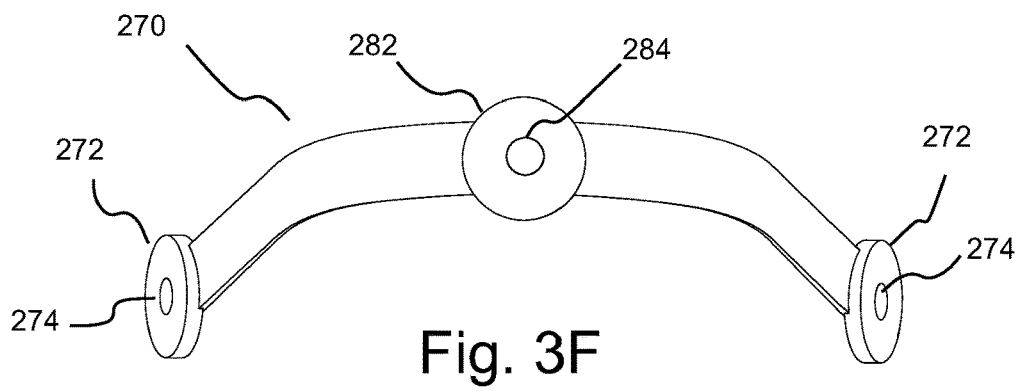
FIG. 3F illustrates a front view of an embodiment of an extending elastomeric member of the system of FIG. 3A.
Figure 3G:
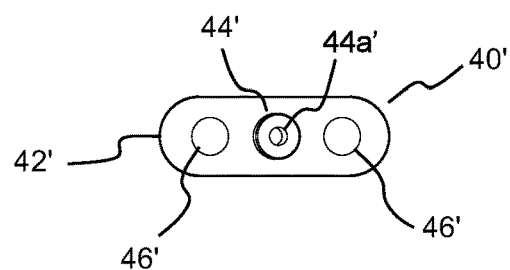
FIG. 3G illustrates an embodiment of a mounting structure for use in connection with the upper dental member of the system of FIG. 3A.

FIG. 2A through 2N illustrates an embodiment of an oral orthotic device or system 100 formed using system or subsystem 10. System 100 includes upper dental member 20 and lower dental member 30 as described above for subsystem 10. One of posterior mounting structures 40 is formed within or embedded within upper dental member 20 in a posterior (or rearward) and buccal or outer position on each side thereof. Likewise, one of posterior mounting structures 40 is formed within or embedded within lower dental member 30 in a posterior (or rearward) and buccal or outer position on each side thereof.

An extending connector system such as a rod assembly 120 is connected between upper dental member 20 and lower dental member 30 at a buccal or outer position on each side thereof. In the illustrated embodiment, rod assembly 120 is operatively connected to upper dental member 20 via one of connectors 50, which is attached to the rearwardmost connector seatings 44 of posterior mounting structures 40 attached to each outer side of upper dental member 20. Each rod assembly 120 is also operatively connected to lower dental member 30 via one of connectors 50, which is attached to the forwardmost connector seating 44 of posterior mounting structures 40 attached to each outer side of lower dental member 30.

In the illustrated embodiment, each rod assembly 120 includes a first end or pivot member 130, a second end or pivot member 150 and an intermediate extending member or rod 170 which extends between first end member 130 and second end member 150. First end member 130 includes a connector section 132 including a passage 134 through which one of connectors 50 passes to connect first member 130 to posterior mounting structure 40 of lower dental member 30. Passage 134 is dimensioned to have an inner diameter slightly larger than the outer diameter of section 56 of shaft 52 of connector 50 so that first member can pivot about shaft 52. Passage 134 may, for example, be dimensioned such that there can be some "play" in the pivoting of first member 130 about shaft 52.

First member 130 further includes a generally cylindrical extending seating section or sleeve 136 including a generally cylindrical opening 138 to receive a first end 172 of intermediate extending member 170. A radially inward extending portion 140 contact first end 172 of intermediate extending member 170 to position intermediate extending member 170 and to prevent first end 172 from exiting first member 130. In the illustrated embodiment, passage 134 is in general alignment with a passage 142 formed in connector section 132 of first member 130, which has a reduced radius as compared to passage 138. The reduced radius of passage 134 is, for example, equivalent to the radius of the opening defined by radially inward extending portion 140. Passage 142 provide access to an adjustment mechanism or connection 174 formed in first end 172 of extending intermediate member 170.

Similar to first member 130, second member 150 includes a connector section 152 including a passage 154 through which one of connectors 50 passes to connect second member 150 to mounting structure 40 of upper dental member 20. Passage 154 is dimensioned to have an inner diameter slightly larger than the outer diameter of section 56 of shaft 52 of connector 50 so that second member can pivot about shaft 52. Passage 154 may, for example, be dimensioned such that there can be some "play" in the pivoting of second member 150 about shaft 52.

Second member 150 further includes a generally cylindrical extending seating section or sleeve 156 including a generally circular opening 158 to receive a second end 176 of intermediate extending member 170. Opening 158 is in connection with a generally cylindrical passage of extending seating section 156, which includes a threaded section 160 to cooperate with a threaded section 178 of extending intermediate member 170 to adjust the distance between first member 130 and second member 150 and thereby the extent to which a patient's lower jaw or mandible is, for example, moved forward relative to the patient's upper jaw. In the illustrated embodiment, adjustment mechanism 174 includes a slot which can, for example, cooperate with a screw driver or similar tool to rotate intermediate extending member 170 and adjust the distance between first member 130 and second member 150 (via the cooperation of threaded section 178 of extending intermediate member 170 and threaded section 160 of extending seating section 156 of second member 150. Adjustment of or titration of system 200 can be performed via adjustment mechanism 174 while system 200 is in place in a patient's mouth to adjust the position of the mandible to varying extents.

In the illustrated embodiment, passage 134 of first member 130 and passage 154 of second member 150 are offset from the axes of extending seating section 136 and extending seating section 156 respectively. Thus, the pivot axes of first member 130 and second member 150 are offset from the longitudinal axis of extending intermediate member 170 (see, for example, FIG. 2D). This offset arrangement can assist in maintaining rod assembly 120 more parallel to the dental arch thereby conforming better to the morphology or conformation of the patient's mouth (as compared to an embodiment wherein the pivot axes are in alignment with the longitudinal axis of extending intermediate member 170).

FIGS. 3A through 3E illustrate another embodiment of an oral orthotic system 200 including upper dental member 20 and lower dental member 30 in which elastomeric tension is used to apply a forward force to the mandible. In the embodiment of system 200, lower dental member 30 is formed in the same manner as described above in connection with oral orthotic system 100. In that regard, lower dental member of system 200 includes one of posterior mounting structures 40 embedded within a posterior and buccal position on each side thereof.

Unlike system 100, however, upper dental member 20 of system 200 need not (but may) include posterior mounting structures 40 embedded within a posterior and buccal position on each side thereof. In the illustrated embodiment, upper dental member 20 includes a single anterior (or forward) mounting structure 40' embedded within an anterior and generally central position thereon. Mounting structure 40' includes one or more connector seatings 44' (one in the illustrated embodiment) along the length of an extending member 42' thereof. As described in connection with anterior mounting structure 40, connectors seatings 44' includes a passage 44a', which may, for example, be threaded to cooperate with a threaded connector such as connector 50. Extending member 42' includes one or more openings or passages 46' into which polymeric material flows during molding to enhance the structural bond or connection of extending member 42' with the polymeric material of upper dental member 20.

In system 200, one or more extending elastomeric members or bands extend between lower dental member 30 and upper dental member 20 to apply force to lower dental member 30 to position and/or stabilize the mandible. In the illustrated embodiment, a single extending elastomeric member 270 is used. Extending elastomeric member 270 includes connecting sections 272 at each end thereof to form a connection with posterior mounting structures 40 on each side of lower dental member 30. In the illustrated embodiment, connecting sections 272 include a passage 274 through which a connector such as one of connectors 50 may pass to connect extending elastomeric member 270 to lower dental members 40 via one of passages 44a of connector seatings 44. In the illustrated embodiment, connectors 50 are connected to the rearwardmost connector seatings 44 on each side of lower dental member 30. Extending elastomeric member 270 further includes an intermediate connecting section 282 (generally centrally positioned thereon in the illustrated embodiment), which includes a passage 284 formed therein. A connector such as one of connectors 50 passes through passage 284 to connect connecting section 282 of extending elastomeric member 270 to threaded opening 44a' of connector seating 44' of mounting structure 40'.

Extending elastomeric member 270 may, for example, be less prone to become disengaged (for example, during installation or removal) than embodiments wherein separate elastomeric members or band are used. Moreover, extending elastomeric member 270 is readily and relatively quickly connectable while in the mouth of the patient. In that regard, lower dental member 30 may, for example, be placed in the mouth of the patient connecting sections 272 connected to connectors 50 on each side thereof. Upon placement of upper dental member 20 in the mouth, the patient may simply extend intermediate connecting section forward to connect intermediate connecting section to connector 50 extending forward from anterior mounting structure 40'.

As clear to one skilled in the art, varying numbers and types of extending elastomeric members (formed, for example, from an elastomeric polymeric material such as urethane, silicon, polyvinylchloride and/or other biocompatible elastomers) may be used to apply force to the mandible. Such extending elastomeric members may, for example, be connected to upper dental member 20 via one or more of anterior mounting structures 40' or, for example, via posterior mounting structures 40 (which may, for example, be configured as described in connection with system 100).

As described above, specially-formed extending elastomeric members, or standard orthodontic elastic members may be releasably attached to upper dental member 20 and lower dental member 30 via, for example, connectors 50. Extending elastomeric members of varying properties (for example, varying lengths, thicknesses, widths, and/or moduli of elasticity) may be used to provide an adjustable extent of advancement of the mandible. System 200 enables, for example, matching the elastic force on the mandible to the opposing muscular forces. Elastic force may, for example, adjusted in response to neuromuscular conditioning or other factors. The adjustability of the elastic forces and the degree of freedom of lateral movement of the mandible provides for patient comfort and tolerability of the system. Use of elastic force to position the mandible may also reduce stresses and forces on the teeth and jaw joints as compared to systems including rigid connectors for positioning the mandible.

FIGS. 4A through 4G illustrate another embodiment of an oral orthotic system 300 including upper dental member 20 and lower dental member 30 in which magnetic force is used to position and/or stabilize the mandible. In the embodiment of system 300, upper dental member 20 and lower dental member 30 are formed in the same manner as described above in connection with oral orthotic system 100 to have one of posterior mounting structures 40 embedded within a posterior (or rearward) and buccal or outer position on each side thereof.

In the illustrated embodiment, system 300 includes first lower mount members 320 on each side of lower dental member 20, second lower mount members 340 on each side of lower dental member 20 and upper mount members 360 on each side of upper dental member 20. In the illustrated embodiment, first lower mount members 320 and upper mount members 360 include a magnetic element, a magnetic section or are magnetized over at least a portion thereof such that like poles are adjacent to each other and repel each other. As, for example, illustrated in FIG. 4E, positive poles of the magnetic sections of first lower mount members 320 and upper mount members 360 can be adjacent each other upon assembly such that a repelling force is created between first mount members 320 and upper mount members 360 and the mandible of the patient is positioned and/or stabilized in a predetermined manner (for example, urged to a forward position) as a result thereof. Alternatively, magnetic attraction can be used by positioning a magnetic upper mount member such as upper 360 forward of a magnetic lower mount member such as first lower mount member 320 such that dissimilar poles are adjacent each other.

In the illustrated embodiment, first lower mount members 320 are generally L-shaped and are movably or slidably attached to posterior mounting structures 40 of lower dental member 30 via, for example, one of connectors 50. Connector 50 passes through an extending passage or slot 322 in the side section of first lower mount members 320 so that the position of first lower mount members 320 relative to second lower mounting members 340 can be adjusted (see arrow in FIG. 4C), for example, via a threaded, elongated rod or screw 380 which passes through a passage 324 (which may be threaded) in first lower mounting member 320 and passages 342 (which may be threaded) in second lower mounting member 340. As described further below, screw 380 may be used to adjust the extent to which the mandible may be forced forward. A upper section 326 of first lower mount members 320 extends over at least a portion of the upper surface of lower dental member 30.

Second lower mount members 340 (which are generally L-shaped in the illustrated embodiment) are fixedly attached to posterior mounting structures 40 of lower dental member 30 via, for example, two connectors 50 which pass through passages 346 in side, connecting sections 344 (see, for example, FIGS. 4E and 4F). An upper section 348 of second lower mount members 340 extends over at least a portion of the upper surface of lower dental member 30.

Upper mount members 360 (which are generally L-shaped in the illustrated embodiment) are fixedly attached to posterior mounting structures 40 of upper dental member 20 via, for example, two connectors 50 which pass through passages 364 in side, connecting sections 362 (see, for example, FIGS. 4E and 4F). A lower section 366 of upper mount members 360 extends over at least a portion of the lower surface of upper dental member 20.

Referring, for example, to FIGS. 4E and 4F, like (positive, in the illustrated embodiment) poles of magnetic sections of first lower mount members 320 and upper mount members 360 are positioned adjacent each other upon assembly. As described above, the resultant repelling force between first mount members 320 and upper mount members 360 forces/ maintains the mandible of the patient in a forward position. Adjusting screw 380 to draw first lower mount member 320 closer to second lower mount member 340 results in greater forward movement of the mandible as a result of the repulsive forces between the magnetic sections of first lower mount members 320 and upper mount members 360.

Upper section 348 of second lower mount member 340 may, for example, be formed of or include a material (for example, a ferromagnetic material) that is magnetically attracted to the magnetic section of upper mount member 360 to, for example, maintain the patient's mouth in a predetermined conformation or range of conformations. For example, lower section 366 of upper mount member 360 and upper section 348 of second lower mount member 340 (and/or other mount members) may, for example, be positioned relative to each other (for example, via adjustment in thickness thereof) to provide a predetermined distance between the patients upper and lower teeth.

Figure 4A:
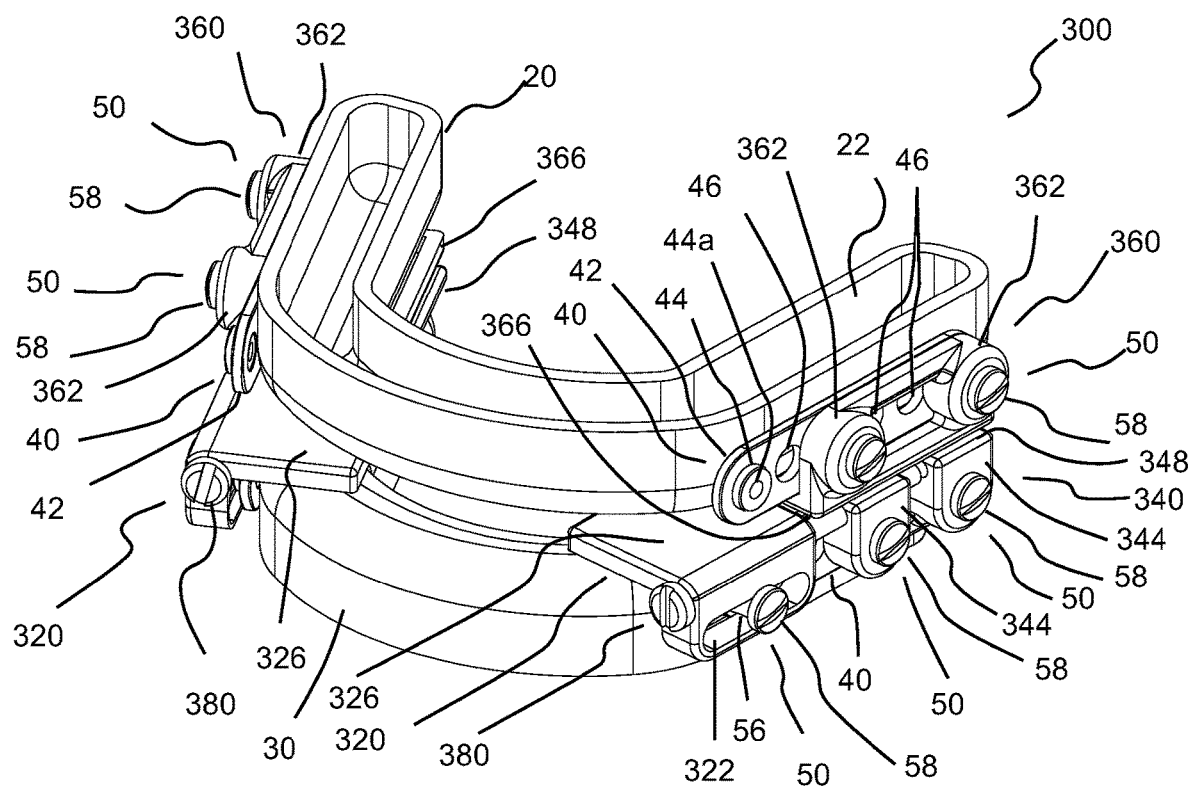
FIG. 4A illustrates an upper, perspective view of another embodiment of an oral orthotic system for treatment of sleep-disordered breathing in which magnetic force is applied to position and/or stabilize the lower jaw or mandible by forcing the lower jaw or mandible forward.
Figure 4B:
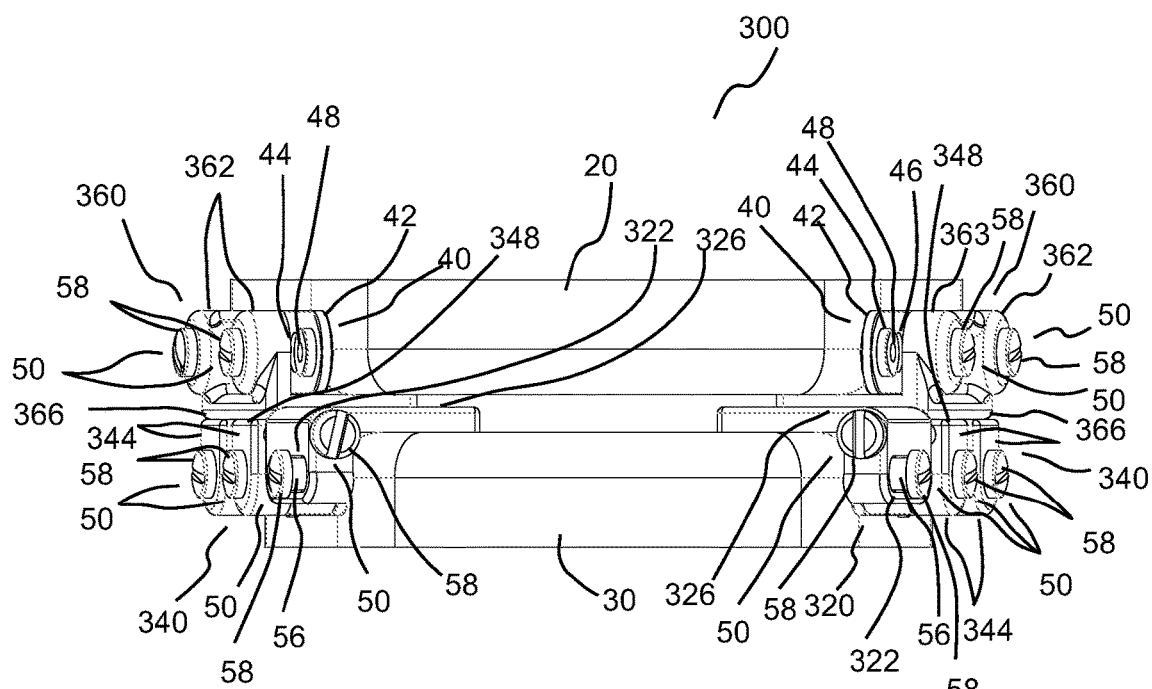
FIG. 4B illustrates a front view of the system of FIG. 4A.
Figure 4C:
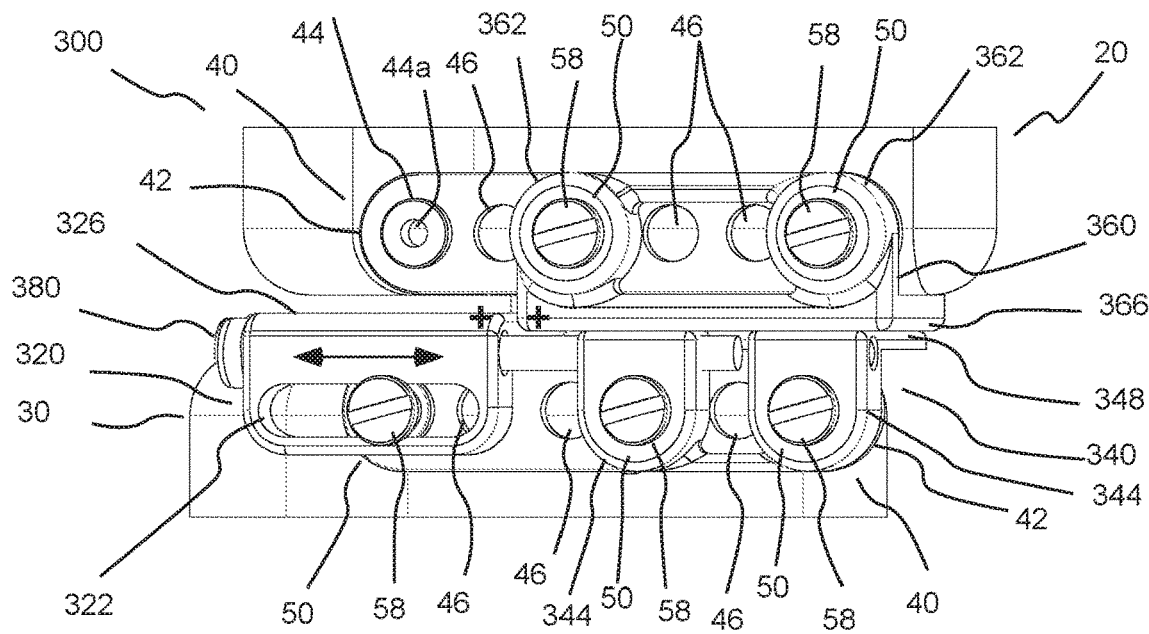
FIG. 4C illustrates a side view of the system of FIG. 4A.
Figure 4D:
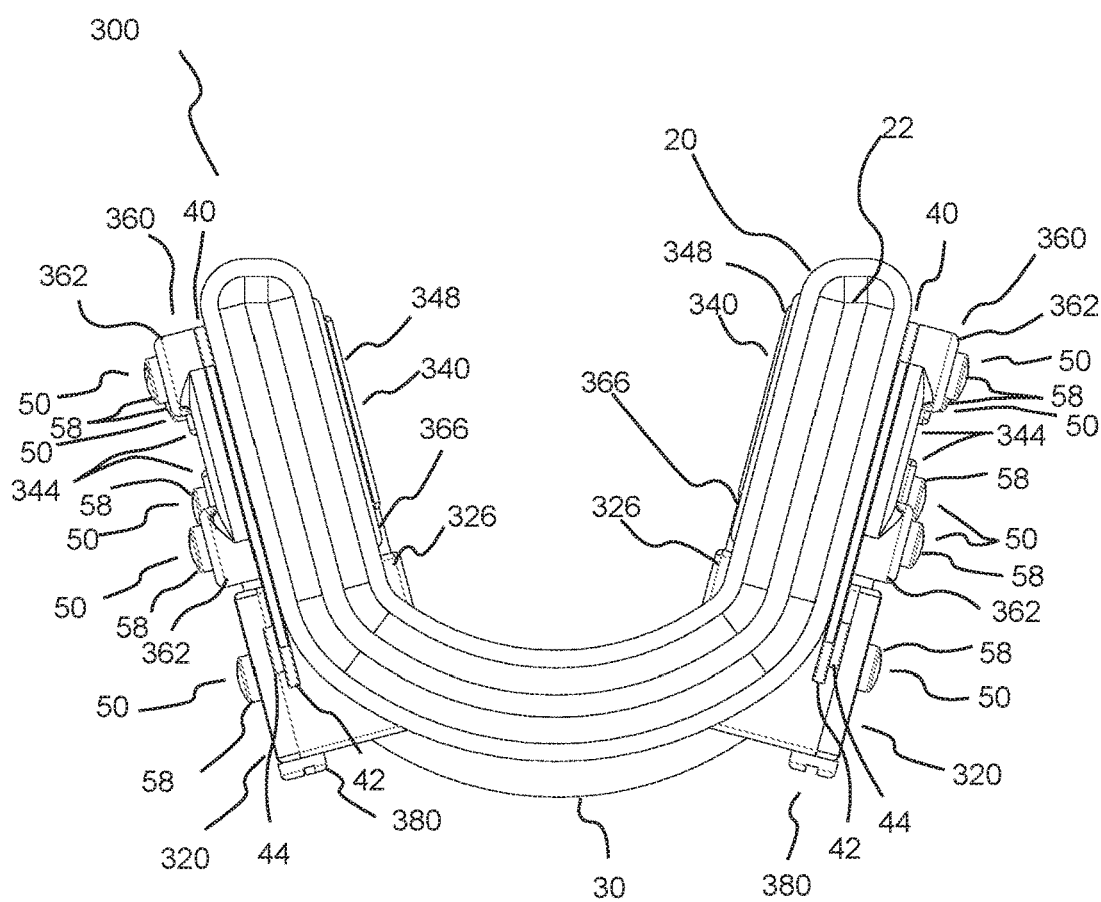
FIG. 4D illustrates a top view of the system of FIG. 4A.
Figure 4H:
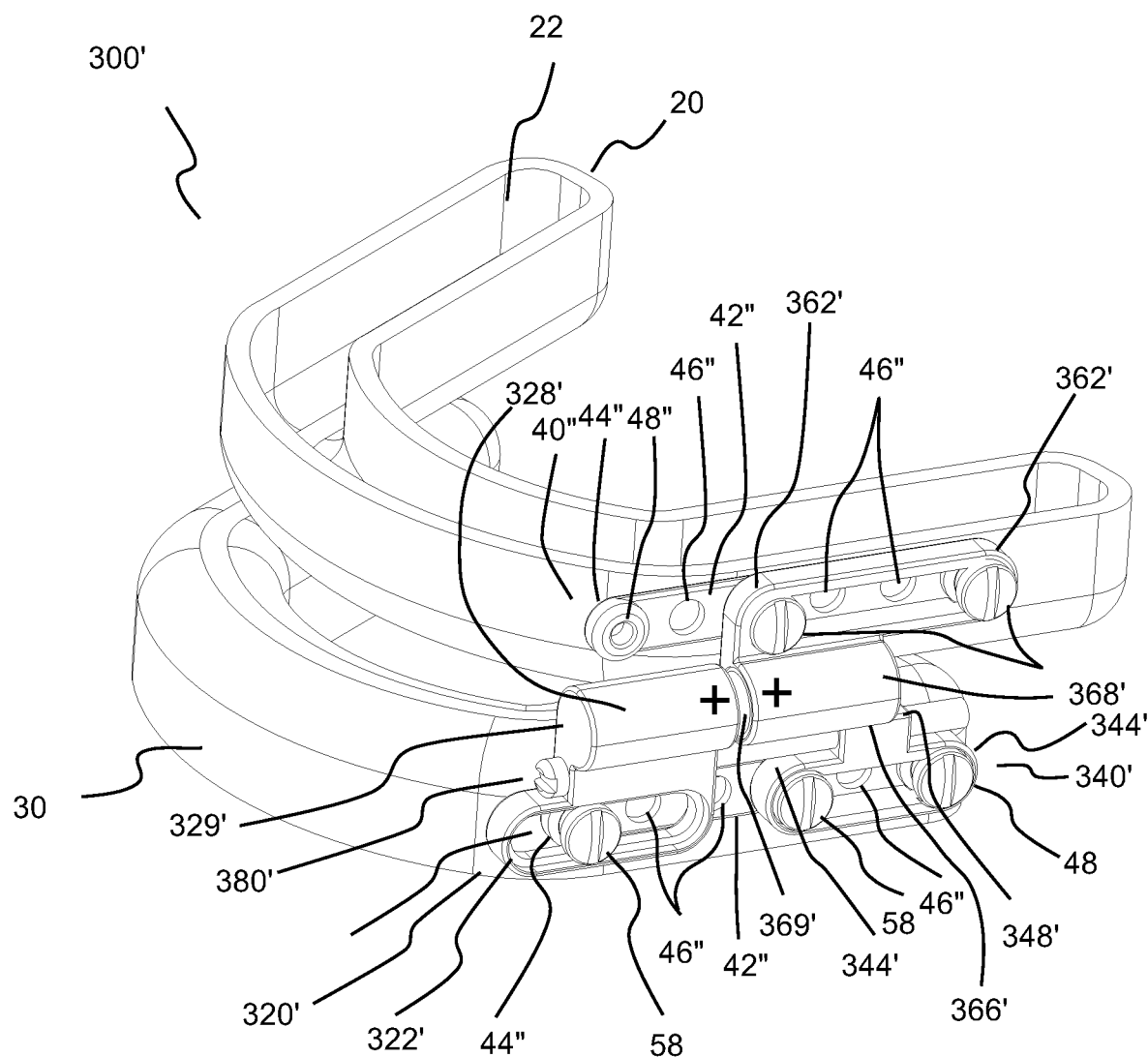
FIG. 4H illustrates an upper, perspective view of another embodiment of an oral orthotic system for treatment of sleep-disordered breathing in which magnetic force is applied to position and/or stabilize the lower jaw or mandible by forcing the lower jaw or mandible forward.

FIG. 4H illustrates another embodiment of an oral orthotic system 300' including upper dental member 20 and lower dental member 30 in which magnetic force is used to position and/or stabilize the mandible. Oral orthotic system 300' is similar in design and operation to oral orthotic system 300 and components of system 300' are numbered similarly to like or corresponding components of system 300 with the addition of the designation "'" thereto. As compared to components of system 300, components of system 300' may, for example, have a less-protruding or lower profile and a less-angled profile to, for example, minimize any patient discomfort. As described in connection with system 300, first lower mount member 320' includes a section 328' including a magnetic component 329', and upper mount member 360' includes a section 368' including a magnetic component 369'. In the illustrated embodiment, magnetic components 329' and 369' are oriented relative to each other so that like poles (positive poles in the illustrated embodiment) are positioned adjacent to (or next to but spaced from) each other to result in a repulsive force therebetween.

Posterior mounting structure 40" of system 300 is very similar in design and operation to posterior mounting structure 40 and components of posterior mounting structure 40" are numbered similarly to like or corresponding components of posterior mounting structure 40 with the addition of the designation "''" thereto. Extending member 42" of posterior mounting structure 40" is reduced in height as compared to extending member 42 of posterior mounting structure 40.

Upper and lower mount members hereof may, for example, be used to provide a predetermined distance between the patients upper and lower teeth in any embodiment of an oral orthotic system hereof. Such upper and lower mount members may, for example, be magnetically attracted to each other to assist in maintaining the predetermined distance.

The upper mount members hereof may be formed to be substantially the same or identical for placement on either side of upper dental member 20. Likewise, the lower mount members hereof may be formed to be substantially the same or identical for placement on either side of lower dental member 30.

Any number of devices or systems may, for example, be attached to the systems hereof via, for example, posterior mounting structures 40, anterior mounting structures 40' and cooperating connectors such as connectors 50. FIGS. 5A and 5B, for example, illustrate a lip seal 400 which may, for example, be attached to a system hereof via passages 404 thereof. In that regard, in the embodiment illustrated in FIG. 5A, system 200 includes anterior mounting structures 40' on the anterior or front of each of upper dental member 20 and lower dental member 30 via which lip seal 400 is attached to system 200 via connectors 50. In the illustrated embodiment, lip seal 400 includes a protrusion 410 to provide space for and/or retain the patient's tongue. In other embodiments, protrusion 410 may be absent. Lip seals such as lip seal 400 may, for example, assist in preventing dry mouth, preventing hypersalivation or drooling, and/or provide some measure of tongue retention.

FIG. 6 illustrates a generic device 500 attached to system 200 via a connector 50 which cooperates with a passage (not shown) in device 500. Device 500 may, for example, include a connection mechanism to connected a positive airway pressure or PAP mask to system 200. Device 500 may also, for example, include a connection mechanism to connect to a sleep lab titration mechanism.

Figure 7A:
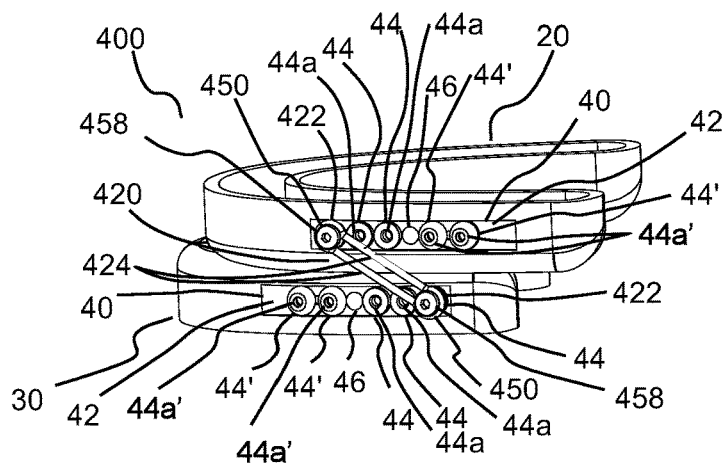
FIG. 7A illustrates an upper, perspective view of another embodiment of an oral orthotic system for treatment of sleep-disordered breathing in which a rigid link positions and/or stabilizes the lower jaw or mandible in a forward position.
Figure 7B:
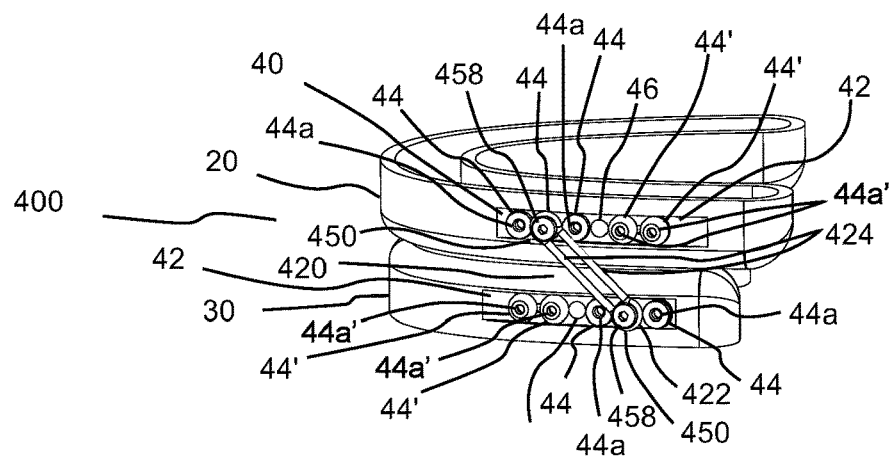
FIG. 7B illustrates another upper, perspective view of the oral orthotic system of FIG. 7A in which the rigid link has been adjusted to position the lower jaw in a more rearward position than illustrated in FIG. 7A.
Figure 7C:
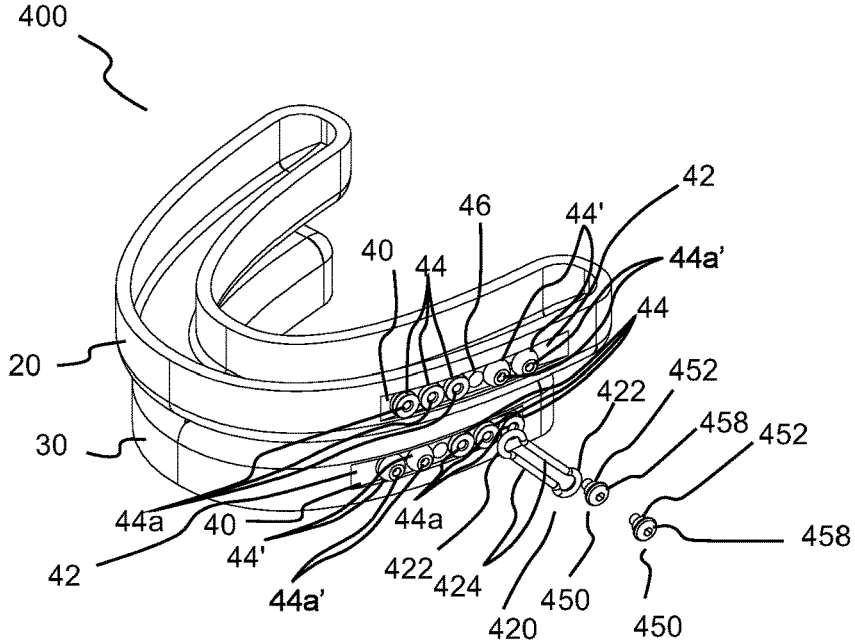
FIG. 7C illustrates a perspective exploded or disconnected view of the oral orthotic system of FIG. 7A.

FIGS. 7A through 7C illustrates another embodiment of an oral orthotic system 400 which may, for example, be formed using the universal system 10 hereof. System 400 includes an extending connector system in the form of a link assembly or rigid link 420 which is, for example, connected between upper dental members 20 and lower dental member 30 at a buccal or outer position on each side thereof. Rigid link 420 may, for example, be formed integrally or monolithically from a rigid material or materials such as metals and/or polymeric materials. Rigid links 420 include arced end or connecting sections 422 through which connectors 450 (for example, shoulder screws) may pass to connect rigid links 420 to upper dental member 20 and lower dental member 30. Rigid links 420 also include extending members 424 which extend between connecting sections 422. In the illustrated embodiment, extending members 424 are spaced apart from each other sufficiently closely such that a shaft or a shoulder or flange 452 thereon (not shown in FIGS. 7A through 7C) of connectors 450 cannot pass there between, thereby maintaining connectors 450 in cooperative connection with connecting sections 422.

Connecting sections 422 of rigid link 420 may, for example, be slipped over a shoulder 452 of connectors 450 before installation of connectors 450 or passed/snapped over heads 458 of connectors 450 after installation. In that regard, extending members 424 have sufficient resiliency to enable expansion of connecting sections 422 (via an increase of the distance between extending members 424) to enable connecting sections 422 to pass over heads 458. Once connecting sections 422 pass over heads 458, extending sections 424 return to their original conformation (or separation distance) so that connecting sections 422 capture shoulders 452 of connectors 450. Providing "snap-over" connectivity may, for example, provide improved ease of user. In that regard, on or more connectors 450 may be provided in connection with each of upper and lower mounting structures 40, and the user may simply choose an appropriate rigid link 420 for quick installation (for example, while upper dental member 20 and lower dental member 30 are in the mouth of the user) by snapping connecting section 422 over heads 458 of the appropriate connectors. The inside diameter of connecting sections 422 of rigid links 420 may be slightly larger than, for example, a shoulder of connectors 450 to provide some amount of free movement in all directions including rotation. Rigid links 420 prevents jaw movement beyond the desired range by preventing the lower jaw from moving in a posterior direction. In that regard, rigid links 420 provide a load in either tension or compression which prevents such movement. In FIGS. 7A through 7C, rigid links 420 are illustrated as being connected to a forward connector 450 on upper dental member 20 and a rearward connector 450 on lower dental member 30, resulting in a load in tension. The orientation of rigid link 420 can be reversed, wherein rigid links 420 are connected to a rearward connector 450 on upper dental member 20 and a forward connector 450 on lower dental member 30, to provide a load in compression.

The overall length of rigid links 420 may be chosen to effect a desired position. System 400 may be removed to interchange rigid links 420 of differing length to adjust jaw position. Links 420 may be coded (for example, by color) to provide ease of selection. Additional adjustment is provided beyond the length range of links by attaching rigid links 420 to connectors 450 (for example, shoulder screws) positioned in different seatings 44/44' in mounting structures 40. In FIG. 7A, rigid link 420 is operatively connected to upper dental member 20 via one of connectors 450. In FIG. 7A rigid link 420 is attached to the forwardmost connector seatings 44 of posterior mounting structures 40 attached to each outer side of upper dental member 20. Each rigid link 420 is also operatively connected to lower dental member 30 via one of connectors 450, which is attached to the rearwardmost connector seating 44 of posterior mounting structures 40 attached to each outer side of lower dental member 30. In FIG. 7B, the relative positions of upper dental member 20 and lower dental member 30 are altered compared to FIG. 7A by connecting rigid links 420 to connector seatings 44 adjacent to the forwardmost connector seatings 44 on upper dental member 20 and to connector seatings 44 adjacent to the rearwardmost connector seatings 44 on lower dental member 30.

Rigid links 420 may, for example, provide increased comfort as compared to rod assembly 120 described above. In that regard, the multiple extending members 424 of rigid links 420 distribute any load upon the cheek of the user as a result of contact therewith over an increased area as compared to rod assembly 120. Rigid links 420 may, for example, be formed generally as a loop from, for example, an integral section or length of a resilient material such as a metal or a polymeric material.

Figure 8A:
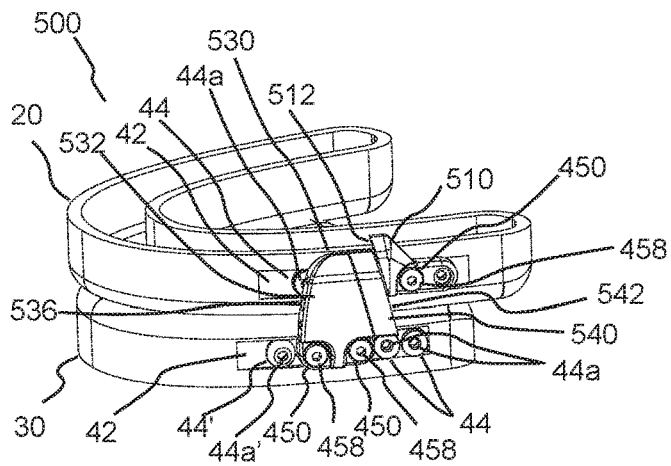
FIG. 8A illustrates an upper, perspective view of another embodiment of an oral orthotic system for treatment of sleep-disordered breathing in which abutment systems are adjusted to position and/or stabilize the lower jaw or mandible in a forward position.
Figure 8B:
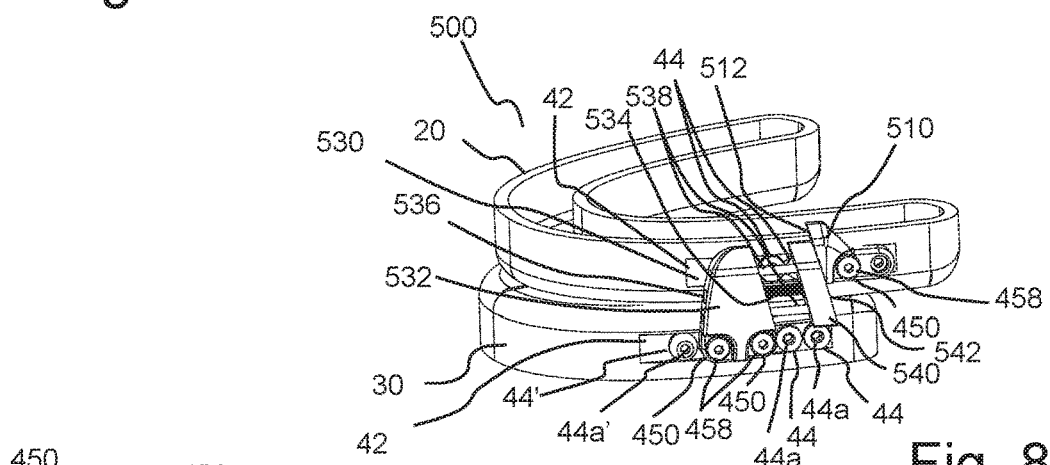
FIG. 8B illustrates another upper, perspective view of the oral orthotic system of FIG. 8A in which a forward, adjustable abutment system has been adjusted to position the lower jaw in a more forward position than illustrated in FIG. 8A.
Figure 8C:
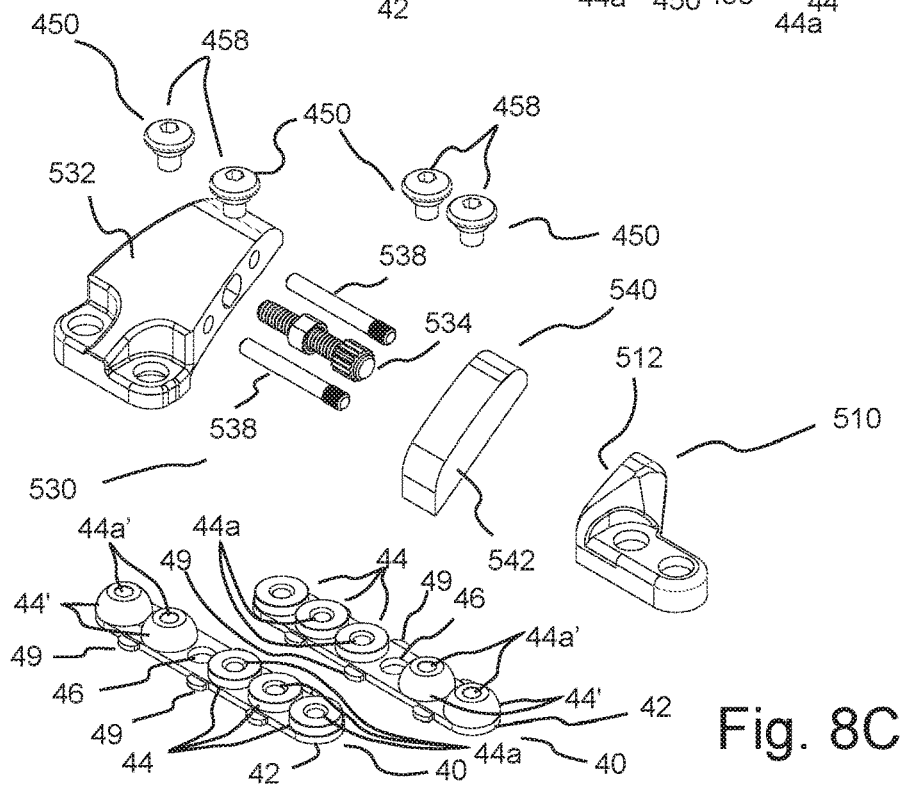
FIG. 8C illustrates a perspective exploded or disconnected view of the oral orthotic system of FIG. 8A.

FIGS. 8A through 8C illustrates another embodiment of an oral orthotic system 500. System 500 includes generally symmetrical left and right rigid or stationary abutment systems 510 mounted on upper dental member 20 and generally symmetrical left and right adjustable abutment systems 530 mounted on lower dental member 30. Abutment systems 510 are mounted to upper dental member 20 via connectors 450 (for example, screws) rearward of adjustable abutment systems 530 (which are connected to lower dental member 30 via connectors 450). Each adjustable abutment system 530 includes a stationary section 532 mounted to lower dental member 30 and a movable section 540, which is movably mounted to the stationary section 532. Movably section 540 includes an angled abutment surface 542 which abuts a similarly angled abutment surface 512 of stationary abutment system 510. The position of moveable section 540 relative to stationary section 532 is, for example, adjusted via an adjustment screw 534, which is accessed via a passage 536 on a forward end of stationary section 532. One or more guide members 538 may, for example, be provided to assist in guiding movable section 540 in a generally linear and parallel manner, while also preventing rotation (about the axis of adjustment screw 534).

As illustrated in a comparison of FIGS. 8A and 8B, rearward movement of movable section 542 via adjustment screw 534 causes lower dental member 30 to move forward relative to upper dental member 20. System 500 may be adjusted in the patients mouth over the full range of adjustment screws 534 on the left hand and right hand sides of the patient's mouth, via access passage 536, which enables a practitioner to insert a tool to turn adjustment screw 534. Interchangeable movable sections 540 of different sizes may be provided to accommodate adjustment greater than the length of adjustment screw 534 provides. In that regard, if the full range of adjustment screw 536 is reached, system 500 may be removed from the patient's mouth to exchange movable sections 540.

System 500 prevents lower jaw movement rearward of a desired range via physical or mechanical abutment as described above. In that regard, abutment surface 512 of stationary abutment system 510 (which is in operative connection with the upper jaw via upper dental member 20) contacts abutment surface 542 of adjustable abutment system 530 (which is in operative connection with the lower jaw via lower dental member 30), preventing additional movement of the lower jaw in the posterior direction. Angles abutment surface 512 and 542 provide for relatively smooth movement with generally uninterrupted contact as the jaw is opened and closed.

As illustrated in FIGS. 7A through 8C, in a number of embodiments, mounting structures 40 include one or more connector seatings 44' (two in the illustrated embodiment) along the length of extending member 42 that are "cup-shaped" or rounded. Like connector seatings 44, connector seatings 44' include passages 44a', which may, for example, be threaded. In the illustrated embodiment, three generally flat connector seatings 44 and two "cup-shaped" or rounded connectors seatings 44' are provided on each mounting structure 40. Cup-shaped connector seatings 44' may, for example, be used in connection with a rod assembly similar to rod assembly 120 that includes corresponding or cooperating "cup-shaped" or rounded connectors to cooperate with connector seatings 44' in the manner similar to a ball joint to better control the motion of the rod assembly relative to mounting structures 40.

As illustrated in FIG. 8C, mounting structures 40 may, for example, include extending tabs 49. Tabs 49 may, for example, assist in securing mounting structures 40 in connection with upper dental member 20 and lower dental member 30.

Figure 9A:
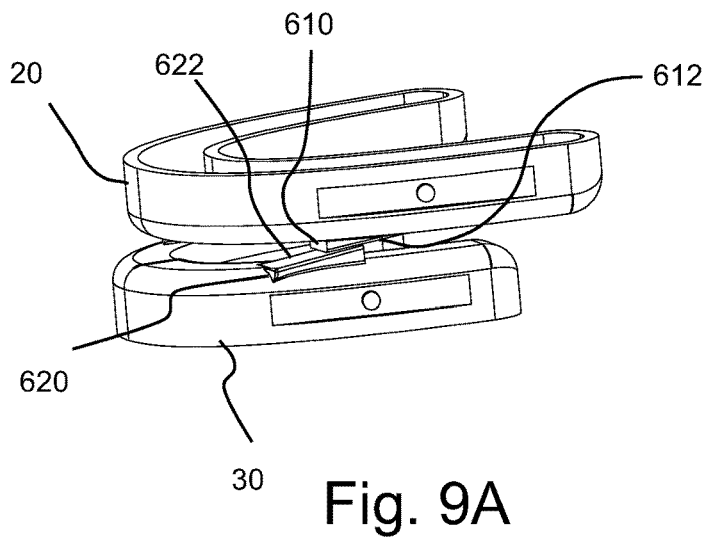
FIG. 9A illustrates an upper perspective view of an embodiment of a system for increasing the gap between the upper and lower jaw with forward movement of the lower jaw, which may, for example, be used with any of the oral orthotic systems hereof.
Figure 9B:
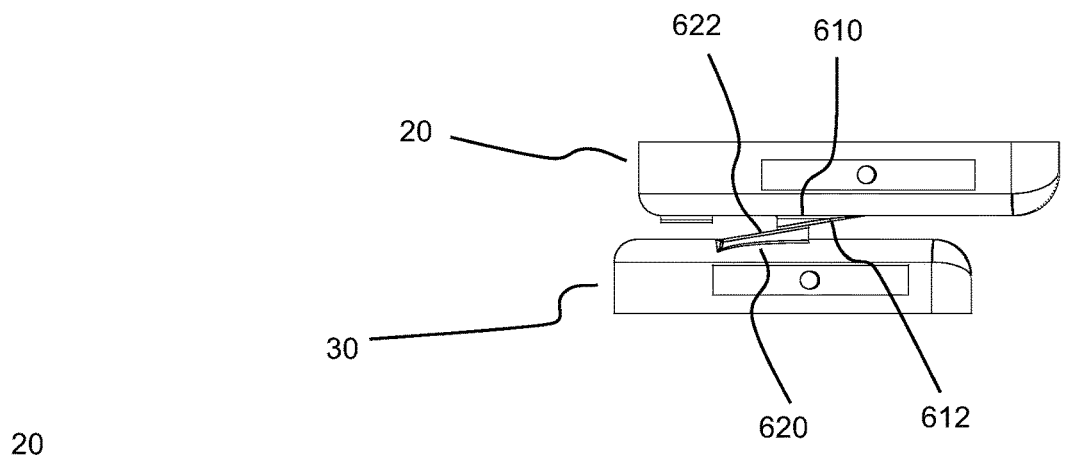
FIG. 9B illustrates a side view of the system of FIG. 9A.
Figure 9C:
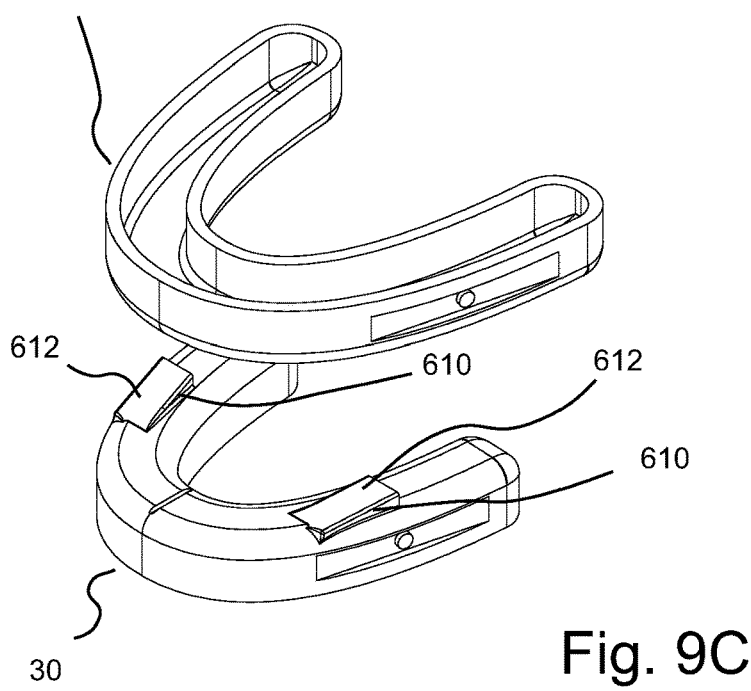
FIG. 9C illustrates another upper perspective view of the system of FIG. 9A.

In any of the systems described herein, ramped, angled or sloped (either linearly or curvilinearly) upper abutment members 610 and ramped, angled or sloped (either linearly or curvilinearly) lower abutment members 620, as, for example, illustrated in FIGS. 9A and 9B, may be attached to upper dental member 20 and lower dental member 30, respectively. Upper abutment members 610 include ramped, angled or sloped surfaces 612 which abut similarly ramped, angled or sloped surfaces 622 of lower abutment members 620. When the lower jaw is moved forward, abutment of sloped surfaces 612 and 622 cause the vertical distance between the upper jaw and the lower jaw to be increased. In the illustrated embodiment of FIGS. 9A through 9C, surface 612 and surface 622 slope upward (toward upper dental member 20 and the upper jaw) as one moves in the posterior direction. In that regard, as lower dental member 30 is adjusted forward relative to upper dental member 20, sloped abutment members 610 and 620 increase the opening between the upper and lower jaw. Abutment members 610 and 620, in connection with the systems described above, provide a combination approach to opening the patients airway with potentially decreased stress on the jaw joint.

Figure 10:
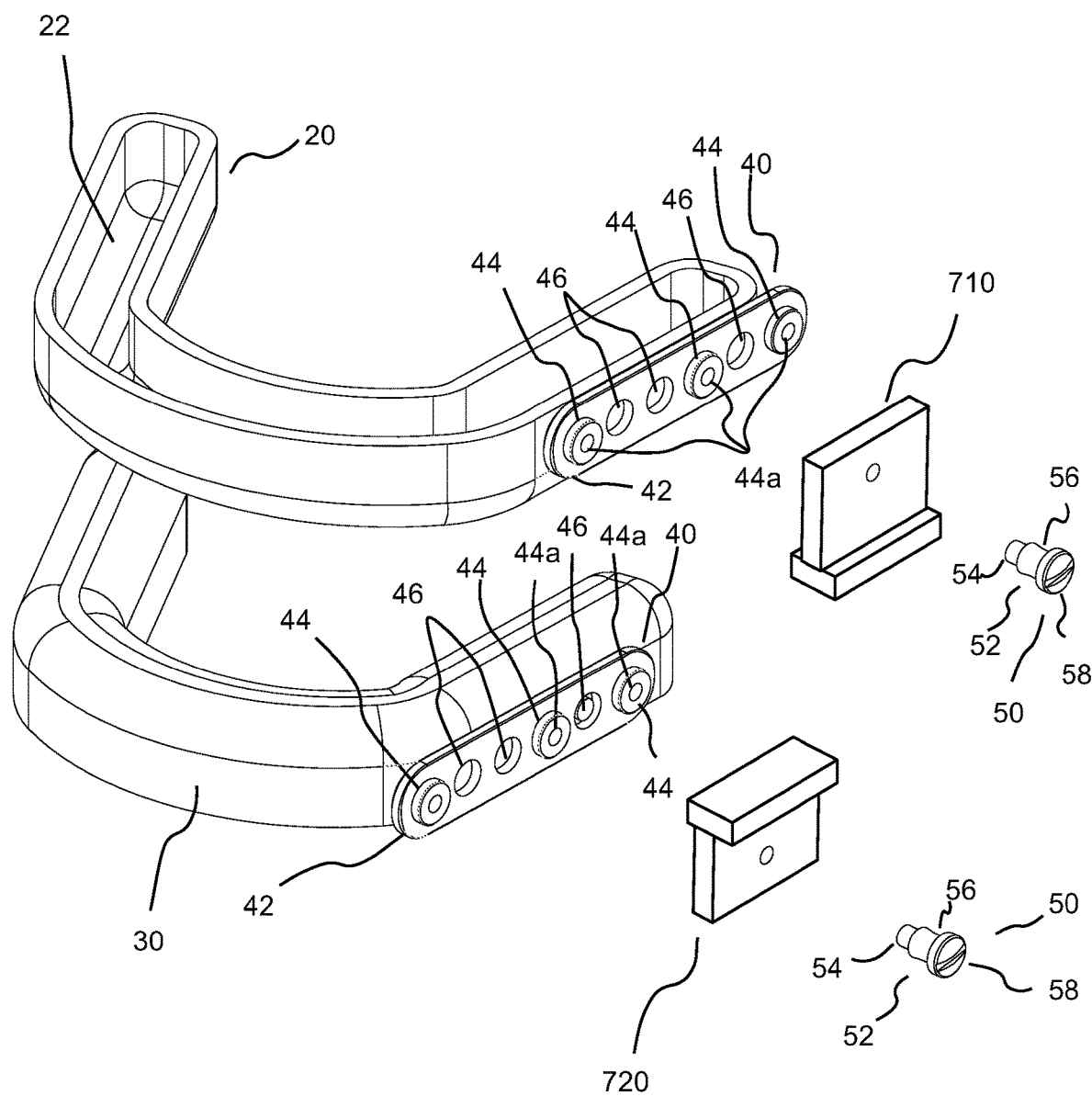
FIG. 10 illustrates an upper perspective view of another embodiment of a system for maintaining a gap between the upper and lower jaw.

FIG. 10 illustrates an upper perspective view of another embodiment of a system for maintaining a gap between the upper and lower jaw. In the system of FIG. 10, an upper abutment member 710 is attached to mounting structure 40 on each side of upper dental member 20 via one or more connectors 50. A lower abutment member 720 is attached to mounting structure 40 on each side of lower dental member 30 via one or more connectors 50. Upper abutment member 710 and lower abutment member 720 are illustrated schematically as block structures in FIG. 10, but can be designed in many different sizes and shapes. Abutment members 710 and 720 may be chosen or adjustable to create a desired gap between upper support 710 and lower support 720. Upper and lower abutment members 710 and 720, respectively may, for example, be provided with ramped surfaces which operate similar to ramped or angled members 610 and 620 described above. Upper abutment member 710 and lower abutment member 720 may, for example, be dimensioned to be used in connection with one or more of the oral orthotic systems described herein.

The foregoing description and accompanying drawings set forth the preferred embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of forming oral orthotic systems to position a mandible of a patient, comprising:
   providing an upper dental member adapted to be placed in connection with upper dentition of the patient;
   providing a lower dental member adapted to be placed in connection with lower dentition of the patient;
   providing a plurality of posterior mounting structures, each of the posterior mounting structures being adapted to be attached to one of the upper dental member or the lower dental member at a posterior, buccal position thereon, each of the posterior mounting structures comprising an extending member;
   wherein force can be applied to the mandible of the patient via a selected one of a plurality of different types of mechanisms via attachment of a first component of the selected one the plurality of different types of mechanisms to one of the posterior mounting structures at one of a plurality of positions thereon and attachment of a second component of the selected one the plurality of different types of mechanisms to another one of the posterior mounting structures at one of a plurality of positions thereon, wherein at least one of the plurality of different types of mechanisms is adapted to push the mandible of the patient forward and at least one of the plurality of different types of mechanisms is adapted to pull the mandible forward.

2. The method of claim 1 wherein each of the posterior mounting structures is formed in substantially the same manner.

3. The method of claim 2 wherein each of the posterior mounting structures comprises a plurality of connector seatings to which one of a plurality of connectors is attachable.

4. The method of claim 3 comprising attaching one of the plurality of posterior mounting structures to the lower dental member at a posterior, buccal position on a first side thereof and attaching one of the plurality of posterior mounting structures to the lower dental member at a posterior, buccal position on a second side thereof.

5. The method of claim 4 comprising attaching one of the plurality of posterior mounting structures to the upper dental member at a posterior, buccal position on a first side thereof and attaching one of the plurality of posterior mounting structures to the upper member at a posterior, buccal position on a second side thereof.

6. The method of claim 5 wherein the plurality of different types of mechanisms comprise a first mechanism comprising at least an elastomeric member, a second mechanism comprising a rod assembly, and a third mechanism comprising an extending link comprising a first arced end and a second arced end and connecting members connecting the first arced end and the second arced end.

7. The method of claim 6 further comprising attaching a first end of the extending link to the first, buccal side of the upper dental member at a first end of the extending link and attaching the extending link to the first, buccal side of the lower dental member at a second end of the extending link, the extending link being adapted to prevent posterior movement of a lower jaw of the patient relative to an upper jaw of the patient beyond a determined range, the extending link comprising a first connecting section at the first arced end thereof adapted to snap over the at least one connector attached to the first buccal side of the upper dental member and a second connecting section at the second arced end thereof adapted to snap over the at least one connector attached to the first buccal side of the lower dental member.

8. The method of claim 7 wherein the extending link comprises a first connecting member attached to a first side of the first connecting section at a first end of the first connecting member and to a first side of the second connecting section at a second end of the first connecting member and a second connecting member attached to a second side of the first connecting section at a first end of the second connecting member and to a second side of the second connecting section at a second end of the second connecting member.

9. The oral orthotic system method of claim 8 wherein the extending link is formed generally in the form of a loop.

10. The method of claim 5 further comprising attaching a first mount member to at least one of the lower dental member and the upper dental member to maintain a predetermined separation between the upper dentition and the lower dentition of the patient.

11. The method of claim 1 wherein the upper dental member and the lower dental member are formed, independently, from at least one polymeric material.

12. A system for forming oral orthotic systems to position a mandible of a patient, comprising:
   a plurality of connectors;
   an upper dental member adapted to be placed in connection with upper dentition of the patient;
   a lower dental member adapted to be placed in connection with lower dentition of the patient;
   a plurality of like posterior mounting structures, each of the posterior mounting structures being adapted to be attached to one of the upper dental member or the lower dental member at a posterior, buccal position thereon, each of the posterior mounting structures comprising an extending member, the extending member comprising a plurality of positions at which one of the plurality of connectors is removably attachable to the extending member; and
   a plurality of different types of mechanisms, each of the plurality of different types of mechanism being configured to apply force to the mandible of the patient via attachment of a first component of a selected one of the plurality of different types of mechanisms to one of the posterior mounting structures at one of the plurality of positions thereon and attachment of a second component of the selected one of the plurality of different types of mechanisms to another one of the posterior mounting structures at one of the plurality of positions thereon, wherein at least one of the plurality of different types of mechanisms is adapted to push the mandible of the patient forward and at least one of the plurality of different types of mechanisms is adapted to pull the mandible forward.

13. The system of claim 12 wherein each of the posterior mounting structures are formed in substantially the same manner.

14. The system of claim 13 wherein each of the posterior mounting structures comprises a plurality of connector seatings to which one of the plurality of connectors is attachable.

15. The system of claim 12 wherein the plurality of different types of mechanisms comprise a first mechanism comprising at least an elastomeric member, a second mechanism comprising a rod assembly, and a third mechanism comprising an extending link comprising a first arced end and a second arced end and connecting members connecting the first arced end and the second arced end.

16. A method of forming oral orthotic systems to position a mandible of a patient, comprising:
providing an upper dental member adapted to be placed in connection with upper dentition of the patient, the upper dental member comprising a first upper posterior mounting structure at a posterior, buccal position on a first side thereof and a second upper posterior mounting structure at a posterior, buccal position on a second side thereof;
providing a lower dental member adapted to be placed in connection with lower dentition of the patient, the lower dental member comprising a first lower posterior mounting structure at a posterior, buccal position on a first side thereof and a second lower posterior mounting structure at a posterior, buccal position on a second side thereof;
wherein force can be applied to the mandible of the patient via a selected one of a plurality of different types of mechanisms via attachment of a first component of the selected one the plurality of different types of mechanisms to the first lower posterior mounting structure and attachment of a second component of the selected one the plurality of different types of mechanisms to the first upper posterior mounting structure, wherein at least one of the plurality of different types of mechanisms is adapted to push the mandible of the patient forward and at least one of the plurality of different types of mechanisms is adapted to pull the mandible forward.

17. The method of claim 16 wherein each of the first lower posterior mounting structure and the second lower posterior mounting structure comprise a plurality of positions at which the first component of the selected one the plurality of different types of mechanisms is attachable and each of the first upper posterior mounting structure and the second upper posterior mounting structure comprising a plurality of positions at which the second component of the selected one the plurality of different types of mechanisms is attachable.

18. The method of claim 16 wherein the plurality of different types of mechanisms comprise a first mechanism comprising at least an elastomeric member, a second mechanism comprising a rod assembly, and a third mechanism comprising an extending link comprising a first arced end and a second arced end and connecting members connecting the first arced end and the second arced end.

* * * * *